(12) United States Patent
Nemenov

(10) Patent No.: US 8,029,553 B2
(45) Date of Patent: *Oct. 4, 2011

(54) PORTABLE LASER AND PROCESS FOR PAIN RESEARCH

(76) Inventor: Mikhall Nemenov, Mountain View, CA (US)

( * ) Notice: Subject to any disclaimer, the term of this patent is extended or adjusted under 35 U.S.C. 154(b) by 397 days.

This patent is subject to a terminal disclaimer.

(21) Appl. No.: 12/011,794

(22) Filed: Jan. 29, 2008

(65) Prior Publication Data

US 2008/0269847 A1  Oct. 30, 2008

Related U.S. Application Data

(63) Continuation-in-part of application No. 10/790,992, filed on Mar. 2, 2004, now Pat. No. 7,402,167.

(60) Provisional application No. 60/898,424, filed on Jan. 29, 2007.

(51) Int. Cl.
    *A61B 18/20* (2006.01)
(52) U.S. Cl. .............................. 607/89; 607/88; 128/898
(58) Field of Classification Search ............ 514/252.04; 128/419, 395, 2, 742, 898; 435/6; 607/89, 607/88

See application file for complete search history.

(56) References Cited

U.S. PATENT DOCUMENTS

| | | | | |
|---|---|---|---|---|
| 3,769,963 A * | 11/1973 | Goldman et al. | ............. | 600/476 |
| 3,900,034 A * | 8/1975 | Katz et al. | ........................ | 607/89 |
| 4,441,507 A * | 4/1984 | Steffin | ........................ | 600/547 |
| 4,592,359 A * | 6/1986 | Galbraith | ........................ | 607/57 |
| 4,671,285 A * | 6/1987 | Walker | ........................... | 607/89 |
| 4,930,504 A * | 6/1990 | Diamantopoulos et al. | ..... | 607/88 |
| 4,985,352 A * | 1/1991 | Julius et al. | ........................ | 435/6 |
| 5,373,853 A * | 12/1994 | Assal et al. | .................... | 600/555 |
| 5,616,140 A * | 4/1997 | Prescott | .......................... | 606/10 |
| 5,755,752 A * | 5/1998 | Segal | ............................... | 607/89 |
| 2002/0002391 A1* | 1/2002 | Gerdes | ............................. | 607/89 |
| 2004/0158300 A1* | 8/2004 | Gardiner | ......................... | 607/88 |
| 2005/0004133 A1* | 1/2005 | Makings et al. | .......... | 514/252.04 |
| 2005/0177093 A1* | 8/2005 | Barry et al. | ..................... | 604/20 |
| 2009/0069871 A1* | 3/2009 | Mahadevan-Jansen et al. | ............................. | 607/89 |

* cited by examiner

*Primary Examiner* — Henry M Johnson, III
*Assistant Examiner* — Jeffrey Lipitz
(74) *Attorney, Agent, or Firm* — John R. Ross; John R. Ross, III

(57) ABSTRACT

A process and laser system for in vitro and in vivo pain research, pain clinical testing and pain management. In preferred embodiments of the present invention a diode laser operating at a 980 nm wavelength is used to produce warmth, tickling, itching, touch, burning, hot pain or pin-prick pain. The device and methods can be used for stimulation of a single nerve fiber, groups of nerve fibers, nerve fibers of single type only as well as more the one type of nerve fibers simultaneously. The present invention is especially useful for research of human/animal sensitivity, pain management, drug investigation and testing, and psychophysiology/electrophysiology studies. The device and methods permit non-contact, reproducible and controlled tests that avoid risk of skin damage. Applicant an his fellow workers have shown that tests with human subjects with the process and laser of the present invention correlate perfectly with laboratory tests with nerve fibers of rats. The device and the methods can be applied in a wide variety of situations involving the study and treatment of pain. Preferred embodiments of the present invention provide laser systems and techniques that permit mapping and single mode activation of C fibers and A-delta fibers.

10 Claims, 19 Drawing Sheets

Example of arbitrary shape laser pulse built from short (such as 1 ms) pulses

Example of standard square wave laser pulses:  FIG. 11
A) Single pulses such as: 1 ms – 60 sec

| Power, W | Pulse duration, ms | Irradiated diameter, mm | Energy, mJ | Energy density, mJ/mm2 | Power density, W/mm2 |
|---|---|---|---|---|---|
| 20 | 10 | 1 | 200 | 255 | 25.5 |
| 16 | 20 | 1 | 320 | 408 | 20.4 |
| 10 | 50 | 1 | 500 | 637 | 12.7 |
| 2 | 500 | 1 | 1000 | 1274 | 2.5 |
|  |  |  |  |  |  |
| 10 | 200 | 2.5 | 2000 | 408 | 2.0 |
| 3.5 | 300 | 2.5 | 1050 | 215 | 0.7 |
| 2 | 500 | 2.5 | 1000 | 204 | 0.4 |
|  |  |  |  |  |  |
| 1.5 | 1000 | 3 | 1500 | 212 | 0.2 |
| 1.2 | 2000 | 3 | 2400 | 340 | 0.17 |
| 1.1 | 20000 | 5 | 22000 | 1121 | 0.06 |

| Number of Pulses | Power, W | Pulse Duration, ms | Irradiated area, mm | Interval between pulses, sec | Energy, mJ | Energy density, mJ/mm2 |
|---|---|---|---|---|---|---|
| 100 | 2.5 | 50 | 2 | 0.35 | 125 | 39.8 |
| 25 | 5 | 300 | 7 | 3 | 1500 | 39 |
| 100 | 10 | 50 | 1 | 60 | 500 | 636.9 |
| 40 | 1.5 | 80 | 2 | 0.15 | 120 | 38.2 |

Burning/Hot pain (accumulation), T = 800 ms, P = 2.5 W

Examples of reproducible pain stimulation and laser induced pain inhibition

| Pulse Duration, ms | Number of applied Pulses | Repetion Rate, Pulse/sec | Total Temperature in irradiated spots, C | VAS pain Intensity Rating on a 1-100 scale |
|---|---|---|---|---|
| 1500 | 1 | 0.1 | 49 | 10 |
| 1500 | 40 | 0.1 | 49 | from 10 to 20 |
| 50 | 1 | 0.1 | 74 | 10 |
| 50 | 40 | 0.1 | 75 | from 10 to 20 |
| 50 | 1 | 0.1 | 75 | 15 |
| 50 | 100 | 4 | 71 | from 10 to 0 |
| 1500 | 1 | 0.1 | 49 | 0 |
| 50 | 1 | 0.1 | 75 | 0 |

FIG 24

Example of application of monitoring of low dose opiod (fentanyl) anesthesia (sedation)

| Time of Laser Tests | Pulse Duration, ms | Number of applied Pulses | Repetion Rate, Pulse/sec | Total Temperature in irradited spot, C | VAS pain Intensity Rating on a 1-100 scale |
|---|---|---|---|---|---|
| initial tests before anestisia | 50 | 1 | 0.1 | 49 | 0 |
| initial tests before anestisia | 50 | 1 | 0.1 | 50 | 0 |
| initial tests before anestisia | 50 | 1 | 0.1 | 74 | 10 |
| initial tests before anestisia | 50 | 40 | 0.1 | 75 | from 10 to 20 |
| initial tests before anestisia | 50 | 1 | 0.1 | 75 | 15 |
| initial tests before anestisia | 1500 | 1 | 0.1 | 47 | 15 |
| initial tests before anestisia | 1500 | 40 | 0.1 | 50 | from 15 to 40 |
| after anesthesia applied | 50 | 40 | 0.1 | 75 | from 5 to 20 |
| after anesthesia applied | 1500 | 40 | 0.1 | 50 | from 0 to 5 |

FIG 25

PORTABLE LASER AND PROCESS FOR PAIN RESEARCH

CROSS REFERENCE TO RELATED APPLICATIONS

This application is a continuation-in-part to U.S. patent application Ser. No. 10/790,992 filed Mar. 2, 2004 now U.S. Pat. No. 7,402,167 and it claims the benefit of Provisional Application Ser. No. 60/898,424 filed Jan. 29, 2007.

FIELD OF INVENTION

This invention relates medical instruments and processes and in particular to instruments and processes for producing pain.

BACKGROUND OF THE INVENTION

Chronic Pain is a Most Serious Problem

Chronic pain places an enormous toll on the human society. Pain syndromes affect more than 30 million Americans per year, costing more than 100 billion dollars in medical expenses and lost work, in addition to the immeasurable expense of human suffering. Unfortunately, currently available means of assessing the pain of these patients are limited in their predictive value in terms of directing treatment regimes.

Prior-Art Research and Medical Devices for Producing Pain

Contemporary basic pain research has a number of significant problems and serious limitations. One of these problems is the inability to create repeatable and reproducible pain stimuli that permit selective activation of particular types of nerve fibers. Progress in pain research has been retarded because of the lack of adequate equipment to test pain sensing nerve fibers in a variety of clinical conditions. In order to obtain statistically proven data during the testing of analgesic drugs in every phase of drug development including clinical trials, it is desirable (and may be necessary) to have objective parameters to estimate the level of pain. If pain could be quantified, this could enormously shorten the time of clinical trials and diagnostics needed to demonstrate statistically significant clinical results.

Pain stimulators currently available on the market in general do not provide adequate stimuli or suffer other deficiencies such as:
  low level of repeatability
  low rate of heating
  inconvenient heat delivery
  lack of quantitative sensory effects
  lack of ability to objectively estimate degree of pain
  lack of ability to produce of single (mono-modal) skin pain sensations as well as other mono-modal skin sensations
  lack of ability to selectively assess pain mediated by the activation of different classes of pain sensing nerve cells Radiant heat stimulators are used in animal pain research. These devices are limited by accuracy of intensity and produce relatively large spots. Heating rates are generally too low to accurately measure very short response times. Some prior art pain stimulators are described in the following patents which are incorporated herein by reference: U.S. Pat. Nos. 5,191,896, 6,248,079, and 5,025,796.

Hot pads can be used as pain stimulators; however, these devices can produce substantial tissue damage in the course of producing the pain.

Ion Channel Research

An important area of nerve research concerns the study of ion channels in the membranes of nerve cells that open and close to regulate nerve impulses include those signaling pain. For heat pain research with nerve cells in vitro, such as experiments concerning ion channels, heat stimuli are typically delivered to cells with a standard perfusion bath apparatus or a Peltier contact heating device. With these devices rates of temperature change are low requiring heat durations on the order of seconds for substantial temperature rises. These instruments can not achieve measurable thermal stimulation of cells in milliseconds. A significantly more rapid stimulus would permit measurements of opening and closing of these channels in response to heat, thereby providing significantly greater insight into the molecular mechanisms of channel activation and regulation.

Use of Lasers

It is known to use lasers for producing pain. Lasers operating at various infrared wavelengths have been utilized in pain research. Lasers provide advantages as compared to radiant heat sources. These are:
  high rate of heating,
  heat for some wavelengths can be delivered by optical fiber, and
  ease of directing laser energy to specific locations.

One problem with many laser sources is that skin damage occurs before or simultaneously with the feeling of pain. Another problem is that laser pulses may produce double sensations that can induce potentials on one type of fiber by suppressing interaction mechanisms between other nerve fibers, for example in spinal cord. This is most frequently seen for laser pulse duration of more than 100 ms. It is known that lasers operating in the range of 980 nm can produce pain in skin tissues. Photons at this wavelength penetrate to about 3.8 mm through skin tissue. Prior art lasers providing pulses with sufficient power to stimulate single nerves are large, heavy and expensive; and therefore not available to many pain researchers.

Nociceptors: A-Delta Fibers and C Fibers

Basic research in pain, analgesia and pharmacology has been accelerating over last several years. One of the results of this work has been the clear demonstration of the differential involvement of different pain sensing nerve cells (called nociceptors). There are two main classes of pain sensing nociceptors in the skin and other peripheral tissue: myelinated A-delta nociceptors and un-myelinated C nociceptors. These nerve cells may also be called nerve fibers. Sensations evoked by activation of these two different nociceptor types are quite distinct. A-delta fiber mediated pain is typically described as sharp, or piercing. C fiber mediated pain, on the other hand, is usually described as burning or aching. There is also a dramatic difference in the latency to pain after activating these two nociceptor types. For example, a rapid pin-prick to a foot can produce two distinct pain sensations: first, a sharp pain which ends when the pin is removed, followed by a second, burning sensation which may be felt well after the needle has left the skin. The first pain is mediated by A-delta nociceptors, and the second pain is mediated by C fiber nociceptors. Thus, activation of these two nerve types has a different meaning to the body. Numerous physiological, anatomical, and pharmacological distinctions have also been described as being distinct between these two nerve types. For example, morphine is much more effective in inhibiting C fiber mediated pain than A delta fiber mediated pain. Included among these is the finding that, with a constant stimulus, such as a wound, A-delta nerve cells respond robustly at first, but then rapidly become to quiescent. On the other hand, C fibers, with the same stimulus, continue to fire continuously. A delta fibers are usually responsible for mediating of sharp pin prick pain and C fibers for warmth sensations and hot/burning pain.

Some chronic pain syndromes, e.g., diabetic neuropathic pain, may be mediated primarily by C fiber activations. Microneurographic studies in patients with painful diabetic neuropathy demonstrate clear increases in sensitivity of unmyelinated (C) nociceptors. Similarly, a preponderance of pain experienced by patients with fibromyalgia is generally associated with C fibers. Conversely, other painful conditions, such as some polyneuropathies and some dental pains appear to be predominately mediated by A-delta nociceptor activation. Thus, the ability to accurately evaluate single C or A-delta fiber function would be useful in both in diagnosis of these diseases as well as for following patient progress. The ability to study a single types of responses (i.e., a C fiber or an A-delta fiber individually) is referred to as "single mode" investigations or "monomodal investigations.

Applicant's Prior Pain Research

Applicant has been conducting pain research using lasers since 1993. In that year he and others successfully developed a protocol for inducing of pricking pain with Cu vapor laser and warmth sensation and hot pain with YAG:Nd laser. During these experiments, a He—Cd laser and a laser diode was also evaluated. The laser diode that was applied had only 600 mW output power and this power level was too small to product effective results. The paper was published in 1994: M. I. Nemenov, L. G. Gladusheva, E. M. Tsirulnikov, I. G. Andreeva. "Thermal and Skin Pain Sensations Due to Laser Irradiation". SPIE Proceeding, v. 2323, p. 537-538, (1994). In 1995, Applicant published a draft calculation of a simple thermal model that compared laser heating and estimates parameters of an ideal pain stimulator. This paper was reported at Laser School in Sicily: M. I. Nemenov, E. M. Tsirulnikov, et al. "Investigation of Skin Sensitivity due to Visible and Near Infrared Laser Radiation", Biomedical Optical Instrumentation and Laser-Assisted Biotechnology, Erice, Sicily, Nov. 10-22, 1995, v. E325, NATO ASI book series, p. 73-80 (1996). Applicant with others conducted additional laser pain experiments in May of 1997 and results were reported in International Workshop: Semiconductor and solid state laser in medicine'97 in St. Petersburg: M. I. Nemenov, E. M. Tsirul'nikov, "Skin Sensation and Laser Radiation as Universal Stimuli", Technical Digest of International Workshop: Semiconductor and Solid State Laser in Medicine 97 and R. A. Suris, M. I. Nemenov. Semiconductor Lasers: Advantages to Medicine., Proceeding of International Workshop: Semiconductor and Solid State Laser in Medicine 97 Russia, St. Petersburg, May 24-25, 1997, pp 3-10; M. I. Nemenov, E. M. Tsirul'nikov, "Laser Tissue Interaction and Skin Sensations", The Fifth Congress of Scandinavian Society for Laser Therapy, Arhus, Denmark, Apr. 4-5, 1997, Technical Digest. Brief result of laser diode stimulator and possible advantages were reported at Second Workshop: Semiconductor and Solid State Laser in Medicine'98 in St. Petersburg: M. I. Nemenov, E. M. Tsirul'nikov "Semiconductor Lasers in Pain and Sensory Research". Technical Digest of the Second International Workshop Semiconductor and Solid State Lasers in Medicine'98, St. Petersburg, May 28-30, 1998. In June of 1998, Applicant successfully developed laser based stimulating device and tested them in Aalborg University. Applicant presented this work in September 1998, showing a new prototype of a 980-nm diode laser device based on 20 W laser module coupled with optical fiber of 420 microns diameter. This work was published: M. I. Nemenov, L. Arendt-Nielsen, "Laser Diodes in Pain research (preliminary study)" Technical Digest of International Symposium on Biomedical Optics Europe '98, Stockholm, Sweden, September 1998, 3570-50. Applicant present the results of research in 1998-2000 research in the following publications: M. I. Nemenov, V. G. Zaitcev, and J. Mikkelsen, "Limitations of Laser Application in Pain Research". Proceeding of $19^{th}$ World Pain Congress, August 1999, Vienna, No. 317 (abstract); J. Nielsen, M. Nemenov et al, Laser diode: "Pain Threshold and Temperature Distribution in Human Skin". Proceeding of $19^{th}$ World Pain Congress, August 1999, Vienna, No. 79 (abstract); M. I. Nemenov, P. F. Bradley et al, "Quantitative Measurement of Laser Evoked Painful Sensations". $20^{th}$ Annual Meeting of American Society for Laser Medicine and Surgery, Reno, Nev., Apr. 5-9, 2000 J. "Laser Medicine and Surgery" (abstract); M. I. Nemenov, W. Greffrath, S. Schwarz, H. Vogel, V. Zaitcev, R.-D. Treede and "A Laser Diode Stimulator for the Study of Cutaneus Pain Sensations", "Laser Evoked Potentials, and Thermal Responses of Primary Nociceptive Neurons" and The $5^{th}$ International Symposium on Pediatric Pain, London, UK, 18-21 Jun. 2000 (Abstract).

What is needed is a better product and process for producing controlled selective quantitative pain. Specifically, there is a need for the development of a small, portable, commercially viable infrared laser stimulator that will permit mapping and differential assessment of pain signals carried by C fibers and A-delta fibers.

SUMMARY OF THE INVENTION

The present invention provides a process and a portable laser system for pain research, pain clinical testing and pain management. A diode laser is used to produce warmth, tickling, itching, touch, burning/hot pain and pin-prick pain with no tissue damage. The device and methods of the present invention can be used for stimulation of a single nerve fiber, groups of nerve fibers, nerve fibers of single type only as well as of different types of nerve fibers simultaneously, all with no damage to skin tissue. The present invention is especially useful for research of human or animal sensitivity, pain management, drug investigation and testing, and in psychophysiology and electrophysiology studies. The device and methods permit non-contact, reproducible and controlled tests that avoid the risk of skin damage. Applicant and his fellow workers have shown that tests with human subjects utilizing embodiments of the present invention correlate perfectly with laboratory test with nerve fibers of rats. The device and the methods can be applied in a wide variety of situations involving the study and treatment of pain. Preferred embodiments of the present invention provide laser systems and techniques that permit mapping and single mode activation of C vs. A-delta fibers.

The diode laser may be used to activate and deactivate heat sensitive nociceptor (s) including: A and C nociceptors, trpv1 positive nerve cells and trpv2 positive nerve cells. The device and process of present invention can be used for investigation and control of central and cortical activation together with functional magneto resonance imaging systems.

The device and method can be used to control local and central anesthesia during surgery procedure as a feedback system together with electroencephalography, magnetoencephalography and functional magnetic resonance imaging. The device and method permit non-contact, non-invasive, reproducible activation (stimulation) as well as deactivation or/and blocking an of single nociceptors or groups of nociceptors in vivo and in vitro.

BRIEF DESCRIPTION OF THE DRAWINGS

FIG. 11 shows examples of single square wave pulses.

FIG. 20A shows currents evoked by repetitive laser stimulation of excised membrane patches of human embryonic kidney cells 293 cells expressing TRPV1.

FIG. 20B shows the kinetics of diode laser induced currents type 2 (TRPV1) and type 4 (TRPV2) expressing nociceptors (laser stimulus: 20 ms, 2.41 W [1.200 mA of laser pumping current]).

FIG. 20C TRPV1 positive (type 2) cells n=8 were activated by laser pulses: 20 ms, output power: 1-6 W, diameter of irradiation area 100-150 microns.

FIG. 22 B shows a dependence of total laser induced temperature (1) and laser power (2) that evoked threshold (0-10 VAS pain Intensity Rating on a 1-100 scale) burning pain on pulse duration of 0.5-2 sec of laser stimulation. The heat rate is: 10-30 C/sec.

FIG. 24 shows a result of application laser of single and repetitive laser stimulation.

FIG. 25 shows results of laser stimulation of pin prick pain (A fibers) 50 ms pulses and burning pain (C fibers) 1500 ms pulses of humans before and after anesthesia intervention with opioid.

DETAILED DESCRIPTION OF PREFERRED EMBODIMENTS

Diode Laser System at 980 nm

Figure 1:
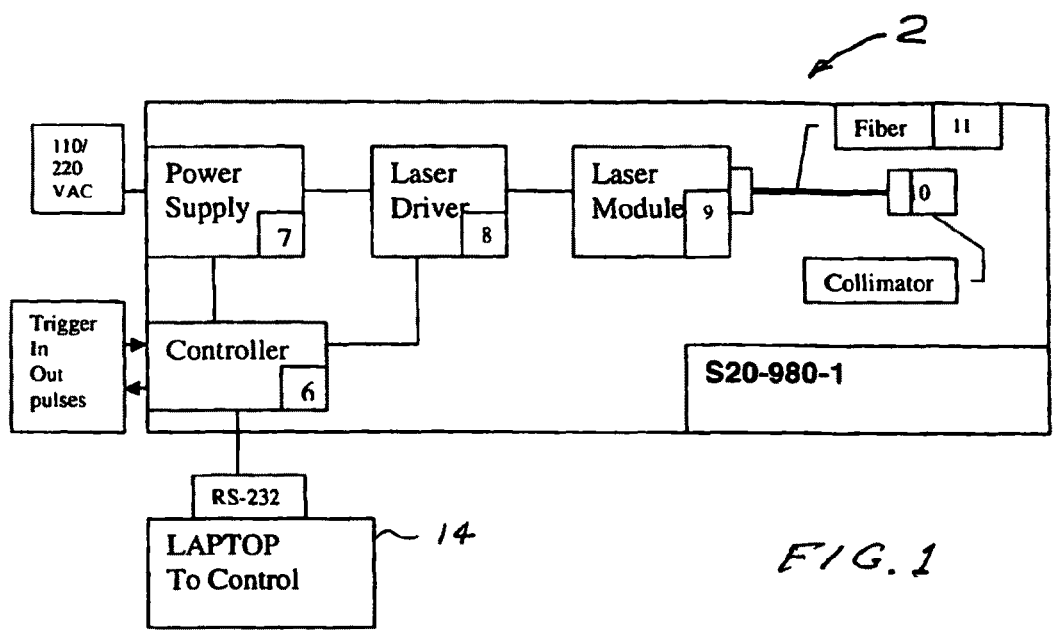
FIG. 1 is a block diagram of a preferred embodiment of the present invention.

A preferred laser system for practicing the present invention is shown in FIG. 1 and is described below. It is a GaInAs/GaAs diode laser system available turnkey as Model No. S20-980-1 form Apollo Instruments Inc. with office located in 18019 Sky Park Circle, Suite F, Irvine, Calif. 92614. The laser system 2 includes: laser module 9 capable of producing up to 30 Watt laser beam as continuous wave or in tailored pulses. The system also includes laser driver 8, laser controller 6, power supply 7, and collimator 10. In addition, the system also includes a 5-mW red aiming diode laser (not shown). The output beam is fed into a fiber coupling and fiber connector with an efficiency of ~80%. The preferred optical fiber has a core diameter 100 microns and numerical aperture of 0.22-11. The laser is operated at wavelength of 980 nm for most experiments of the type described herein. However, other wavelengths in the range of 200 nm to 1.9 microns are available by changing diodes. The laser may also be used as a pump beam to produce other wavelengths. The laser system includes personal laptop computer 14 programmed to provide the following functions:

1) Standard square wave laser pulses:
   A) Single pulses such as: 1 ms-60 sec,
   B) Repeatable pulses such as 1 ms-60 sec with intervals pulses of 10 ms-2000 sec.
2) Arbitrarily shaped laser pulses built from short (such as 1 ms) closely spaced (such as 1 ms intervals) pulses. An arbitrary shape pulse could be single or repeatable. An example is twenty ms 0.5-Watt pulses followed by ten ms 0.75-Watt pulses followed by ten ms 1 Watt pulse followed ten ms 1.5 Watt pulses. Such an arbitrary pulse shape could be useful for experiments to determine the speed at which pain signals travel through particular nerves.

Pulse shapes are discussed in more detail below and are described in FIGS. 10 through 15B.

ADVANTAGES OF THE PRESENT INVENTION

Some of the uses and advantages that the present invention provides are listed below:
- (a) many types pain research humans, animal and an ion channels of cells may be conducted,
- (b) a great variety of pulse shape for activation of A-delta fibers in the range of 20 to 300 ms,
- (c) monomodal pin-prick type pain from threshold to tolerance level without generation of skin lesions.
- (d) mapping of location of nociceptors and skin receptors with a resolution of better than 0.1 mm on the surface and better than 0.05 mm in terms of depth in the skin
- (e) an easy measurement of spatial summation of pricking and burning pain and warmth sensations thresholds in the range of diameters from 0.1-100 mm,
- (f) easy timed measurement of thresholds of pricking and burning pain and warmth sensations in the range 10 ms-20 second,
- (g) reproducible differential activation of C vs. A delta fibers and temperature sensitive ion channels with standard deviation of less than 12%,
- (h) reproducible monomodal warmth sensation stimulation,
- (i) reproducible monomodal burning/hot pain stimulation,
- (j) direct differential measurement of speed conductivity of A delta and C fibers,
- (k) direct test of type of pain/sensation mechanisms (cortical, spinal, peripheral) by application of two optical fiber probes to the same dermatome with different offset (latency) times, (For example, because of difference in the activation/inactivation characteristics of C and A delta fibers, the use of two stimulating probes in the same dermatome of patient/volunteer allow for assessment of the neurological area where disturbances in sensory function originate.)
- (l) controllable heating of tissue with adjustable pulse shape,
- (m) direct activation of ion channels in membranes of isolated cells with spatial resolution up to 0.01 mm and temporal resolution up to 1 ms,
- (n) a diagnostic test of threshold of pain/sensation, temporal and spatial summation of thresholds and pain/sensations to determine of normal and abnormal responses,
- (o) reproducible stimulation and offset measurements of oro-facial areas of cutaneous nociceptors and receptors of humans and animals,
- (p) behavioral tests of rats, mice and monkeys,
- (q) psychophysiological test of humans,
- (r) heat controlled activation of nerve fibers, cells, ion channels,
- (s) selective activation of at least A delta and C fibers cells and ion channels by selection or/and control ramp and shape of heating and cooling, size of irradiated (heated area), location of irradiated area, depth of heating. Depth of heating is selected by changing of lasing wavelength of laser diode (800 nm-1.900 micrometer) and beam size and will depends on type of skin (color, area) or color of cells. Heating rate controlled by measurement temperature on the surface of skin or cell and adjusted by tuning the lasing power or/and pulse duration. The heating control could be provide directly by temperature feedback loop or by using empirically determined standard setting for different skin types,
- (t) investigation of the interference of different or the same types of sensations (activations) by application the same or different stimuli to the same area with tunable time delay and amplitude,
- (u) increasing of power for pulse duration of 50-150 ms from 0.5 W with step of less than 0.2 W for diameter of irradiation area 0.5-2 mm inducing clear monomodal pin prick pain and selective activation of A delta fibers in humans as well as in animals. An exception is the orofacial area where some times A delta terminals are absent in humans or/and animals,
- (v) increasing the pulse duration from 300 ms to 20 sec with a power level of around 1.5 W and diameter of irradiation area between 5 mm-15 mm leads to induction of clear monomodal C fiber hot pain that may or may not follow a warm sensation, and
- (w) increasing the power for pulse duration of 400-2000 ms and diameter of irradiated area 3-5 mm may induce clear monomodal C fiber hot pain or clear monomodal warmth sensation.

Alternative Laser Systems

In another preferred embodiment of the invention a 980-nm laser system is assembled from components available from component suppliers as follows:

Laser Module:
1. Single laser diodes 980 nm are available from JDS Uniphase, Corp. office located in 1768 Automation Parkway San Jose, Calif. 95131,
2. SDL-6380 A, L2, output power 4 W, emitting area 100 microns coupled to standard multimode optical fiber 100/125 microns with numerical aperture (NA) 0.22 by 1.1.7 Fiber coupler, part number 9003.002, LIMO are available from Lissotschenko Mikrooptik GmbH, with offices located in Bookenburgweg 4-8 44319 Dortmund, Germany.
3. Laser diode bars are available from Coherent Inc office located in 5100 Patrick Henry Drive, Santa Clara, Calif. 95054,
4. CW bars part number 1015325 type B1-98-30C-19-30-A coupled to standard multi-mode fiber 100/125 microns with numerical aperture (NA) 0.22 or laser diode CW bars SPL MA98-F are available from OSRAM Opto Semiconductors office located 3870 North First Street San Jose, Calif. 95134
5. Laser modules where single laser diodes or laser bars are coupled to 100/125 microns fiber together with vision pilot lighting are available from the following sources: Laser Modules: Model F20-980-1, Apollo Instruments, Inc. office located in 18019 Sky Park Circle, Suite F, Irvine, Calif. 92614 or/and Model HLU15F100-980, LIMO—Lissotschenko Mikrooptik GmbH, office located in Bookenburgweg 4-8 44319 Dortmund, Germany or/and PUMA-20, QPhotonics L.L.C. office located in 21 Pepperwood Drive, Chesapeake, Va. 23320, Model LASS 20 M, LASMED LLC, 284 Tyrella Ave Suite 10, Mountain View, Calif.
6. Laser diodes are controlled by driver current that transform input voltage amplitude to current and apply this current to laser diode module. The following laser driver are available on the market for 20 W laser diode models: P40-808-6, D-560, Apollo Instruments Inc., LDD-50/100, Lumina Power Inc., or/and 7701A, Analog Modules Inc, LDD50 LIMO—Lissotschenko Mikrooptik GmbH; LASS 20 M, LASMED LLC.

The free tip of the optical fiber can be linked to a collimator to avoid differences in power density as the distance between skin and collimator is changed. The ideal collimator should have a minimum beam size 1-1.5+/−0.1 mm within a range of 10-40 mm and a tunable beam size of 1.5-15 mm. The type of collimator that is available on market permits the decreasing of beam divergence and keep the diameter of spot 1+/−0.1 mm in working distance ~5 mm. Collimators are available (OEM LC-1—fiber connected collimator) from Multimode Fiber Optics Inc. office located in 9A Great Meadow Lane, East Hanover, N.J. 07936 or F230 series of collimators available from Thorlabs Inc., with office in Newton, N.J.

The NA×D is a constant for geometrical optics, where NA—numerical aperture (divergence of beam in radians), D—diameter of core fiber or beam after fiber. Therefore, an increasing of diameter of beam from 0.1 mm to 1 mm permits a decrease in the beam divergence 10 times. This permits to have a beam diameter of +/−0.1 mm for range of 5 mm after collimator.

The above laser systems can produce laser pulses with durations of 1 ms-200 sec with an accuracy of +/−1 ms and power of 50 mW-20 W with an accuracy of +/−0.5%. The several models of controllers as well as turnkey systems that include a laser diode module, laser driver and program controller that comply with these specifications are available on the market: S20-980-1, Apollo Instruments Inc; BWF4, BWTEK office located in 825 Dawson Drive, Suite 1 Newark, Del. 19713. (OEM), as described above. The controller preferably also controls laser current and the temperature of laser diodes inside the laser module and monitors lasing power and set up power and control power and state (switch on/off) of the pilot (aiming) beam.

A set of algorithms are preferably developed to permit use of laser diode system for selective activation of C and A delta fibers. The set may be developed and applied based on laser manufacturers instructions such as those provided with the laser module of DLR series of IPG Photonics Corporation, office located in Oxford, Mass.

Low Cost Testing

An inexpensive way to selectively stimulate A-delta and C fibers with a laser is to use a single laser diode coupled to 100/125 or 60/125 fiber. For example, the SDL-6390-L3 of JDS Uniphase laser with output power of 5 W per 100/125 microns fiber is currently available. It has only one laser diode. The 5 W SDL6390-L3 can stimulate C fibers and wide range of pulse duration and beam size and permit stimulation of A delta fibers in the range of 100-150 ms, and beam size ~0.5-1.0 mm.

Laser Configurations

A 980-nm laser of the type described above can be arranged in a variety of configurations for laboratory research, clinical research, clinical testing or treatment. Some of these configurations are described in FIGS. 1A through 5.

Figure 1A:
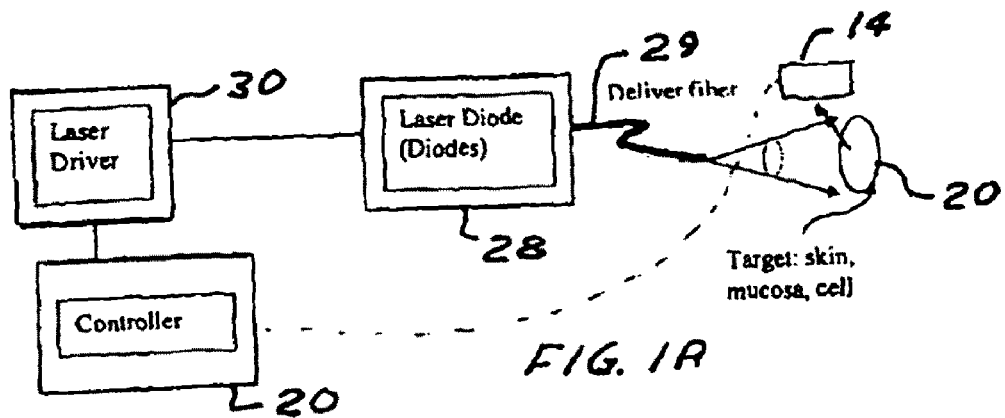
FIGS. 1A, 1B and 1C show various types of laser delivery systems.
Figure 1B:
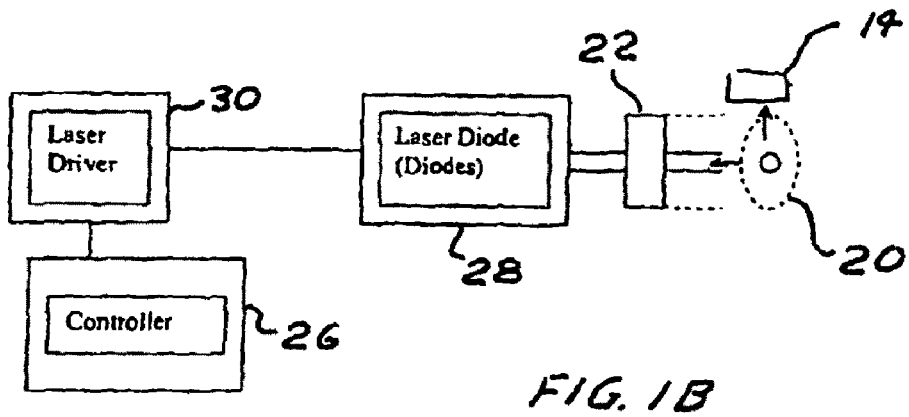
Figure 1C:
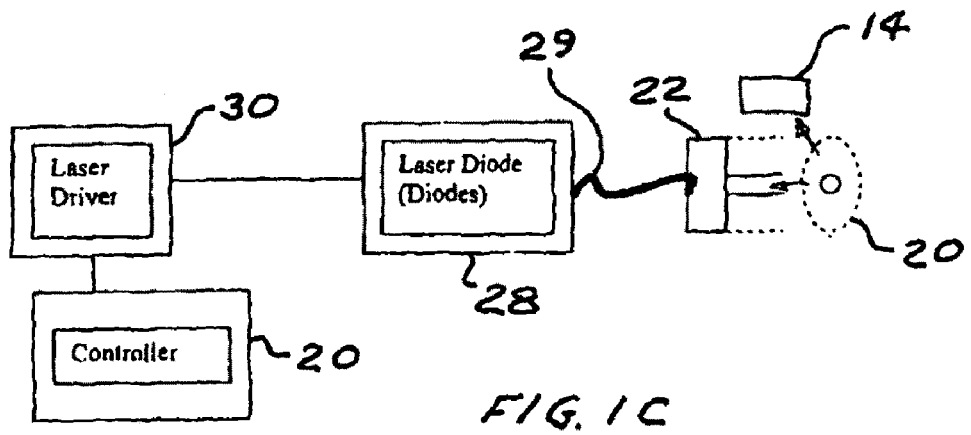

FIG. 1A shows a system in which a fiber optic is used to deliver laser pulses to skin surface 20 with the temperature of the surface being monitored by infrared sensing camera 14 that provides a feedback signal to controller 26 for synchronization of stimulation scan and image recording and monitoring of time interval between applied laser pulse and muscle reflex. FIG. 1B is similar to FIG. 1A except the laser pulses are delivered as a collimated beam using lenses. FIG. 1C combines the pulse delivery features of FIGS. 1A and 1B.

Figure 2A:
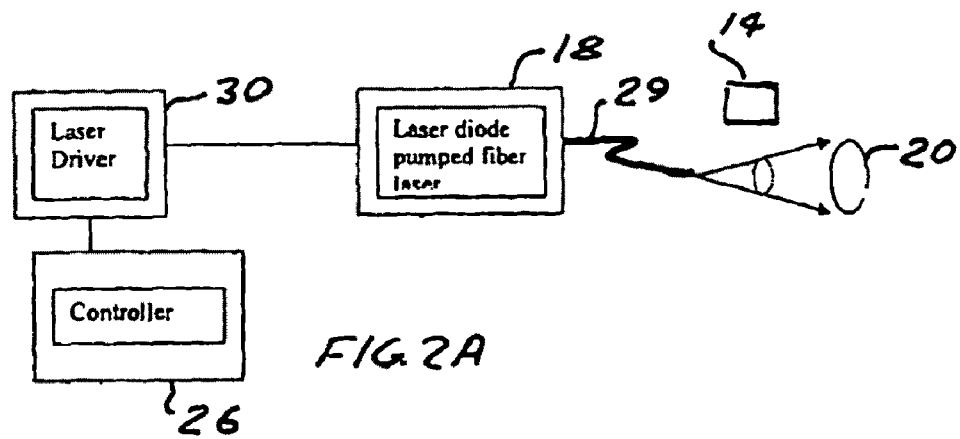
FIGS. 2A-2B show two additional types of delivery systems.
Figure 2B:
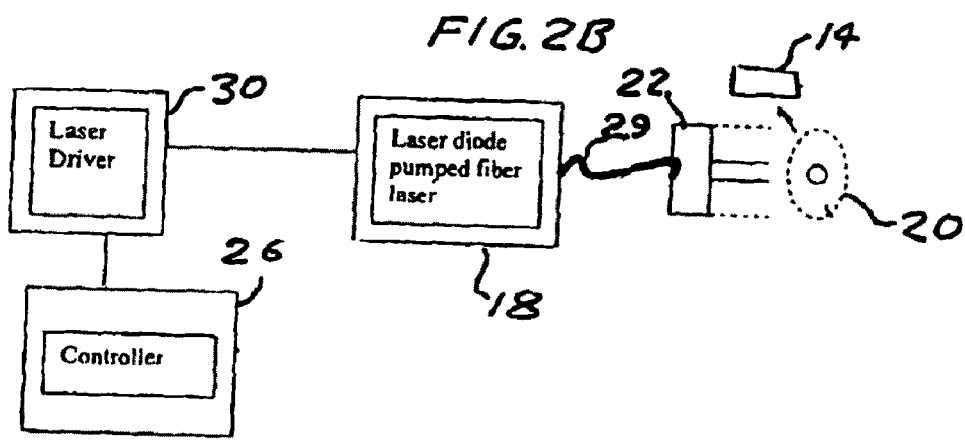

In FIG. 2A an active erbium doped fiber 24 is pumped by the 980 nm laser system to produce 1450 nm laser pulses at the output of the fiber. The preferred fiber is single mode fiber with core diameter 5-15 microns, NA 0.11-0.22. The 1450 nm pulses are used to illuminate skin surface 20 for applications where this longer wavelength pulse energy is desired. This setup is also good for doing activation of ion channels in laboratory experiments. In FIG. 2B the output from fiber 24 is collimated with a tunable collimator 22 to control the diameter of the beam within a range of 1 to 15 microns. An infrared sensing camera 14 in both cases monitors the irradiated spot 20 and records reflexes of the subject.

Figure 3:
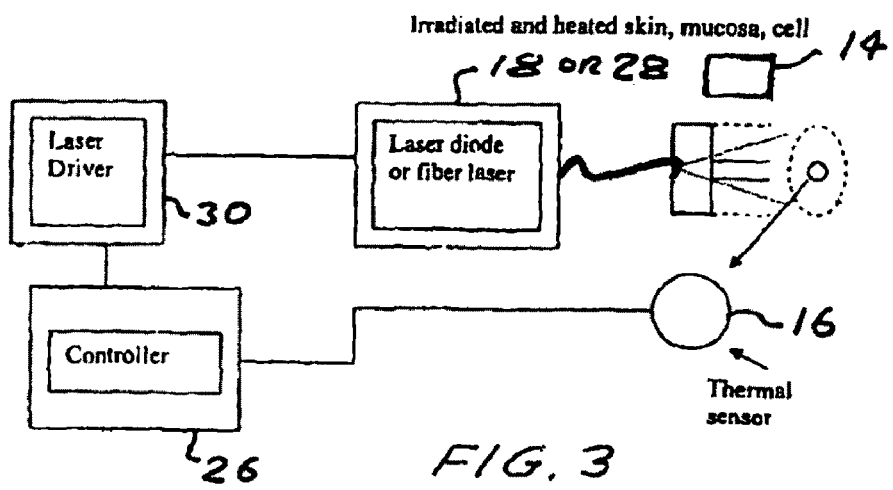
FIG. 3 shows a light delivery system with temperature feedback loop from an infrared thermal sensor.
Figure 4:
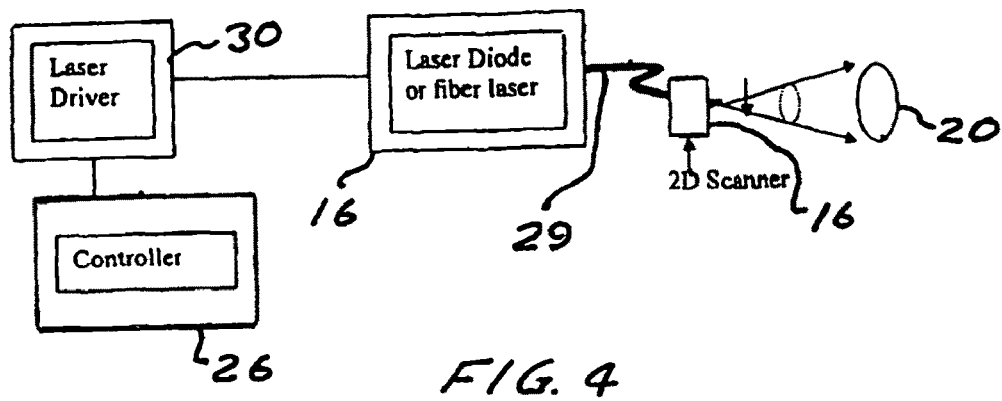
FIG. 4 shows a two-dimensional scanner to map test locations on skin surface.
Figure 5:
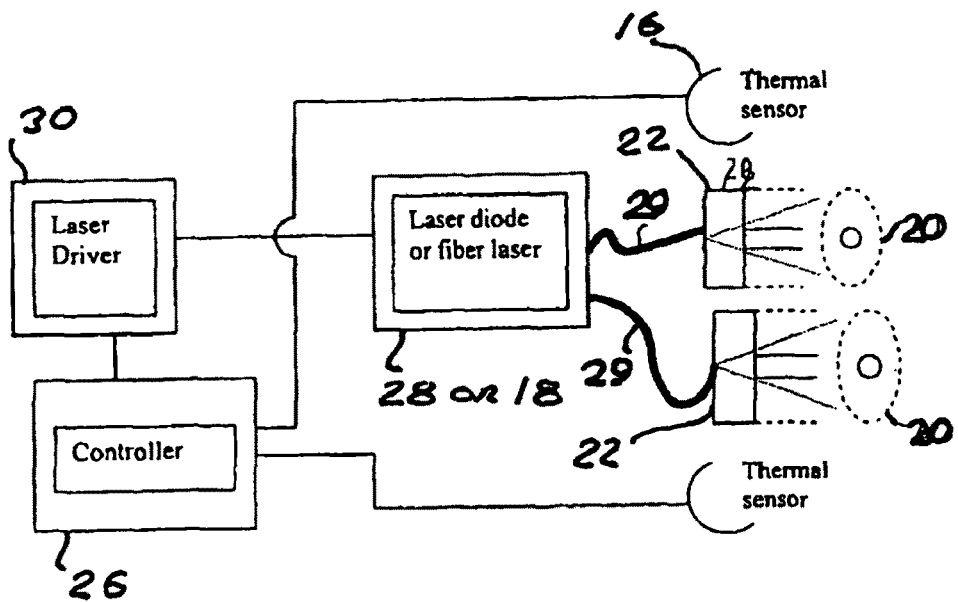
FIG. 5 shows two light delivery systems (two laser probes) to directly measure the speed of conduction of nerve fibers.

In FIG. 3 temperature feedback is provided with thermal infrared sensor 16 that can be used to control the temperature—time profile with a precision of less than 1 millisecond and 1 degree centigrade. In FIG. 4 a two dimensional scanner 16 is used to provide a precise illuminated pattern on a target area 20. Scanners such as Model SCANcube® 7 (available from SCANLAB AG with offices in Cincinnati, Ohio) provides scans with a precision of about 5 mrad. In FIG. 5 a single laser (that could provide either 980-nm pulses or 1450-nm pulses) is used to illuminate two regions at the same time or with tunable time delay. In another embodiment a single controller controls two completely separate laser systems each with its own laser driver. This could be important in experiments when measuring response times to separate pain events.

Figure 6A:
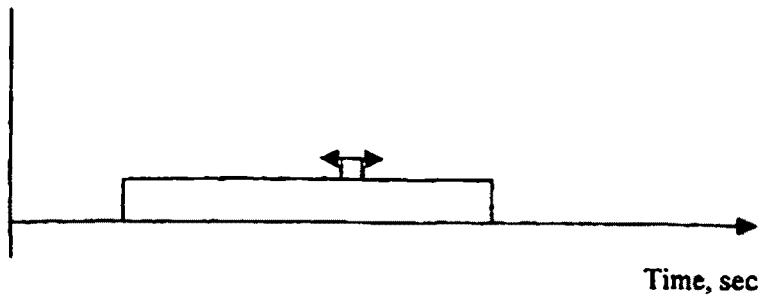
FIGS. 6A and 6B show a technique for testing nerve response using specially tailored laser pulse shapes.
Figure 6B:
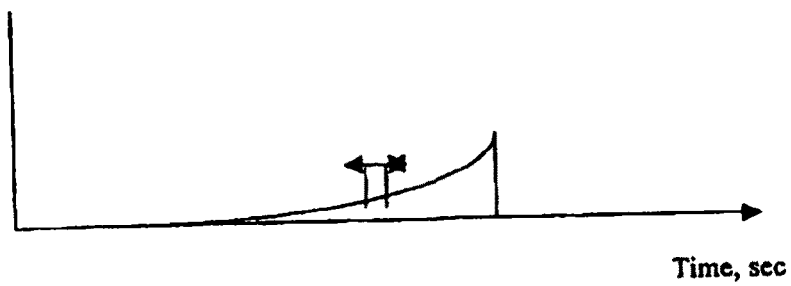

FIGS. 6A and 6B show the type of pulse power profile that is available with the laser system first described above. FIG. 6A shows power vs time and FIG. 6B shows temperature vs time. The purpose here is to gradually heat the skin to a temperature just below the pain threshold and then provide a short pulse to exceed the threshold. With this technique the time of the short pulse providing the threshold energy can be measured with precision, and compared to a reflex or a measured nerve signal to accurately determine nerve transit times and other important information regarding the functioning of the nerves.

Figure 7A:
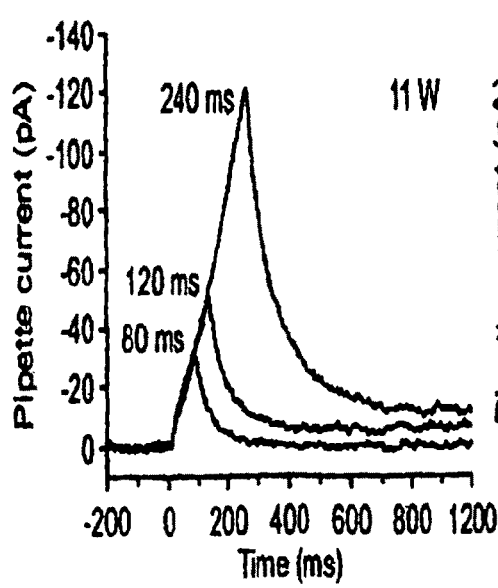
FIGS. 7A and 7B show traces of heat sensitive neurons for various power and pulse durations.
Figure 7B:
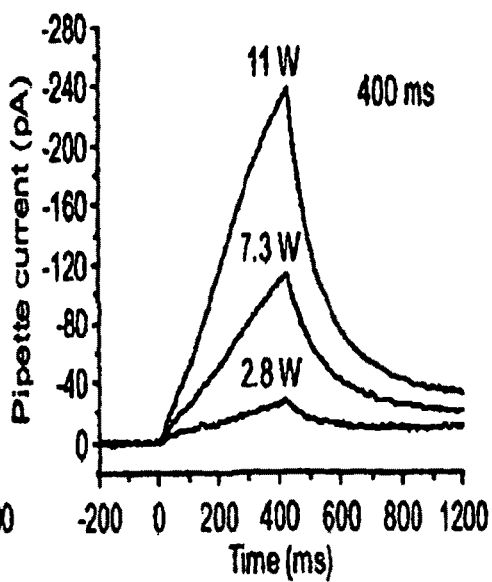
Figures 8A, 8B:
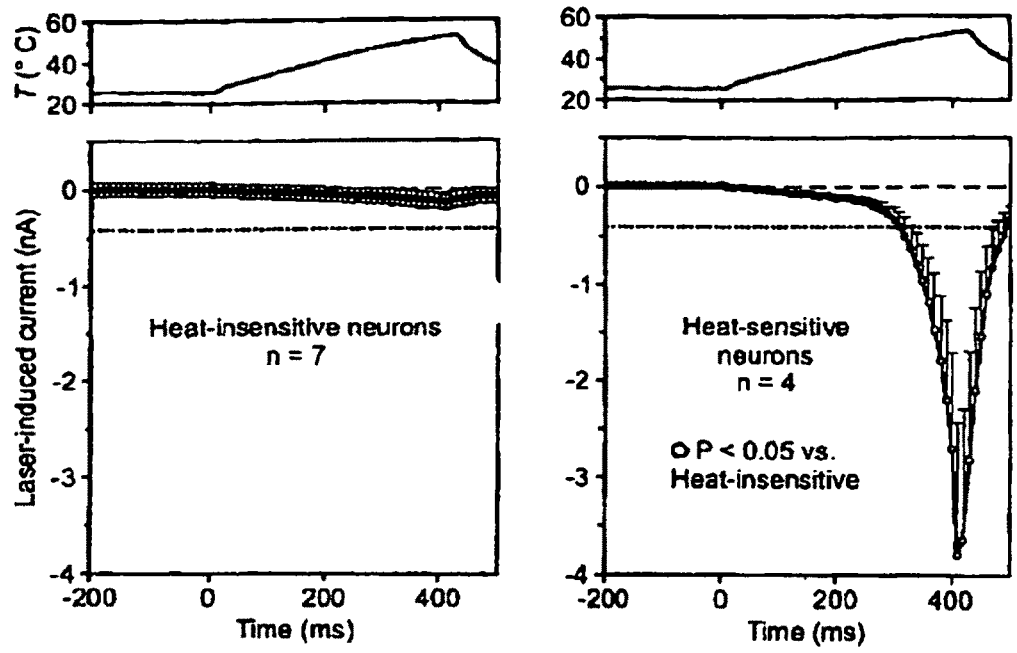
FIGS. 8A and 8B show activation of heat sensitive neurons vs neurons that do not respond significantly.

FIGS. 7A and 7B show heat induced current in a heat sensitive cell from a dorsal root ganglion of a rat. The heat was provided with 1.2-mm diameter, 980-nm, 11-Watt pulses for the time periods indicated. In FIG. 7A the maximum pulse duration was 240 ms, and for the FIG. 7B graph the maximum pulse duration was 400 ms. FIG. 8A shows the results of tests on a neuron that was not heat sensitive. Heat resulted in only a very slight current. FIG. 8B however shows the effect of applying heat in the same amount and under the same conditions to a heat sensitive neuron from a dorsal root ganglion of a rat.

Figure 9:
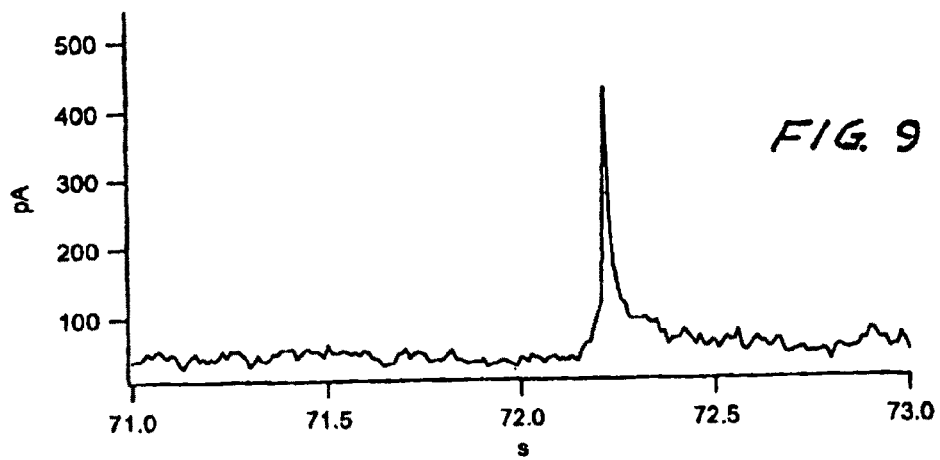
FIG. 9 shows show results of laser heat induced activation of heat sensitive ion channels.
Figure 10:
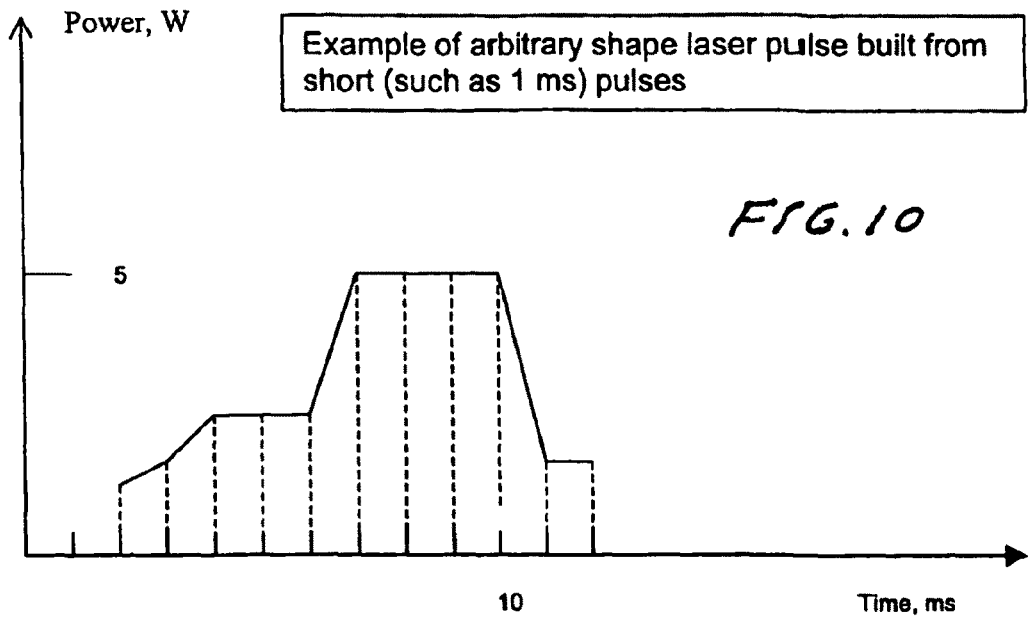
FIG. 10 shows an arbitrary 10 ms pulse shape built from 1 ms pulses.

FIG. 9 shows results of ion-channel experiments performed by Applicant with the above-identified 980-nm laser system. The laser heat induced current of inside-out membrane patches from VR1-expressed HEK293 cells. The cells were stimulated by laser light and electro-physiological responses were recorded using a standard patch-clamp protocol. The laser stimulus evoked TRPV1-mediated currents based on their characteristic current-voltage profile and the absence of such responses in cells not expressing VR1. A trace of the response is provided in FIG. 9. The size of membrane patches was around 10 microns, pulse duration 100 ms, and the size of irradiated area 100 microns.

EXAMPLES OF PAIN TESTING PROCEDURES

Example 1

Pin Prick Pain to Activate A Delta Fibers

It is well known that for heat induced simulation of prick-pain stimulation the temperature of the skin has to be more 46-48 C degree and ramp of heating has to be over 70-100 C degree per second. However, these data were based on pulse durations of more than 300 ms. To the best of Applicant's knowledge, there are not any prior art data in the literature relating absolute temperature and ramp of heating for stimuli duration less than 300 ms. The best, simplest protocol, to access A-delta nociceptors and evoked monomodal pin prick pain is the following:

The best laser set up parameters for lasing of 980 nm:
Pulse duration: 50-150 ms,
Beam size: 0.5-2 mm
Power: 2-20 W
Density of Energy Range: 14 mJ/mm$^2$ The example of practical realization of the combination of pulse duration, beam size and pulse power for threshold pin prick pain stimulation is shown in Table 1:

TABLE 1

Example of Threshold of Single Pin Prick Pain Stimulation (A delta fibers). Irradiated Spot Diameter 0.8 mm, Glabrous Skin

| Pulse, ms | POWER, W | Energy, mJ | Peak Temperature, C. | Energy Density mJ/mm$^2$ | Power Density W/mm$^2$ |
|---|---|---|---|---|---|
| 50 | 9.5 | 475 | 73 | 945 | 18.9 |
| 100 | 4.5 | 450 | 62.5 | 896 | 9.0 |
| 150 | 3.2 | 480 | 58 | 955 | 6.4 |
| 200 | 2.76 | 552 | 57 | 1098 | 5.5 |
| 300 | 2.5 | 750 | 54.8 | 1492 | 5.0 |

Figures 12, 13:
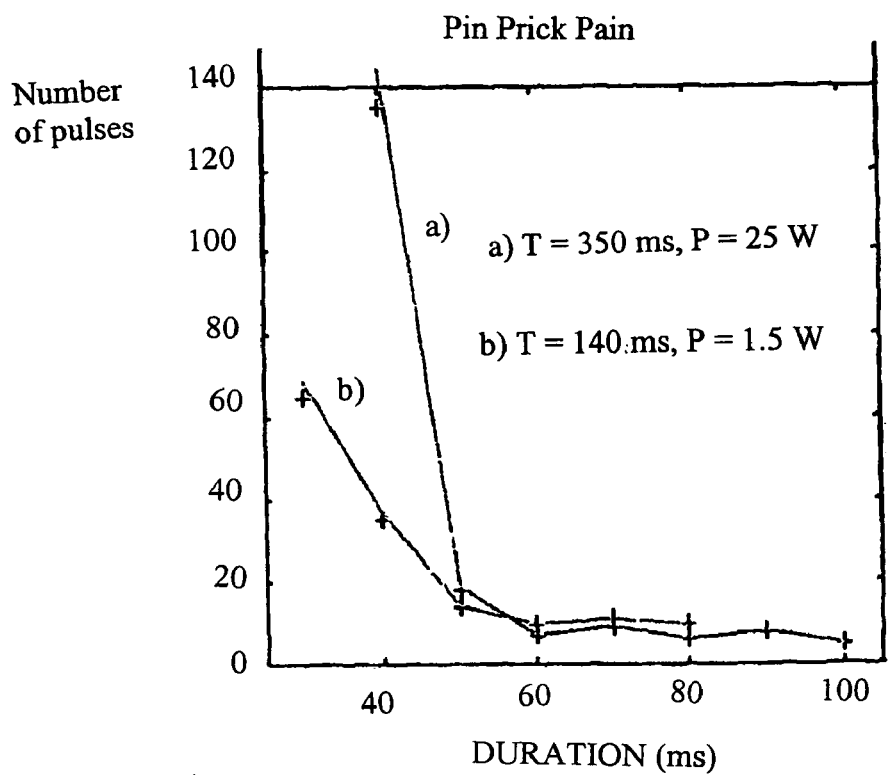
FIG. 12 shows examples of repeating pulses with intervals between them.
FIG. 13 shows simulated threshold pin-prick values for 2.5 Watt and 1.5 Watt pulses with variable numbers of pulses and variable pulse durations.
Figure 16A:
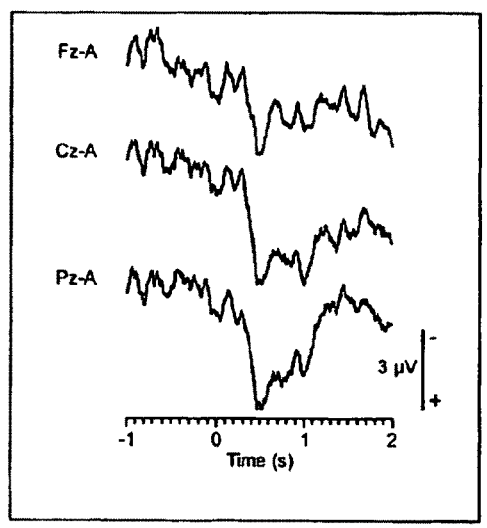
FIGS. 16A and 16B show evoked potentials test data and location of brain wave detectors for pin-prick type pain.
Figure 16B:
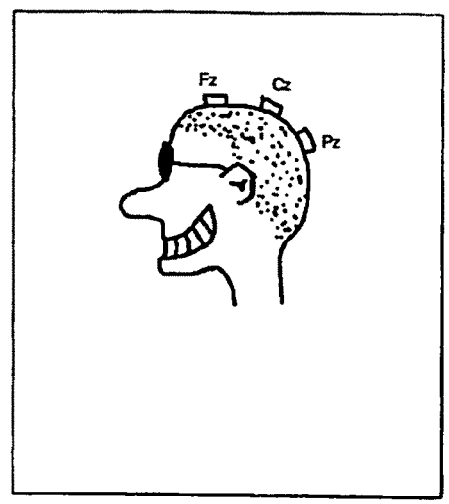

The experiment consisted of the following actions:
1) Collimated beam with a diameter of 2 mm, within a range of power of 5.0-10.0 W and a pulse duration of 100 ms is applied to investigated area of skin to determine the individual sensitivity and to map the location of A delta nociceptors. The pulse power is increased from 5 W with step of 0.5 W until first sensation is evoked. After that the pulse power is fixed and the irradiated spot is scanned within XY frame 5 mm×5 mm to find the location of a nociceptor. Pulse power is applied for each new location—the spatial step is around 0.5 mm for fingertips. The inter-stimulus time is 20 sec.
2) When the location of appropriate spot is determined, the size of collimated beam is adjusted to 1 mm, duration of pulse set up to 50 ms and pulse power is increased from 2 W until the threshold level is achieved. After that, either the power is increased up to tolerance level of pain or power could be increased by 20% (the estimated tolerance level is about 20%-30% above the power to induced threshold pain) and psychophysiology or electrophysiology testing could be done.
3) The step of increasing of power is within the range of 0.1 Watt-1.0 Watt with pulse duration of 300 ms-50 ms.
4) For determining temporal summation curve (Power of Pain Thresholds vs. Pulse Duration), step 2) is repeated with successively longer pulse duration until 200-300 ms is reached (steps of pulse duration 50 ms) or until the first type of evoked sensation with increasing of power will be warmth, burning/hot pain or any other sensation but not pin prick pain.
5) The time interval between applied laser pulses should be more than at least 20 sec-200 sec to avoid cumulative heating of skin or until induced sensation/pain completely disappeared.
6) For determining the number of pulses that evokes threshold of pin-prick type pain, square waved pulses within a range of pulse duration of 10-300 ms and interstimulus delay of 0.1-3 sec are applied. Examples of repetitive pulse application for A delta stimulation are shown in FIGS. 12 and 13.
7) In the case of chronic pain syndromes diagnosis there could be differences between normal skin sensitivity and tender areas. For example, for fibromyalgia syndrome the actions 1-4 are repeated for normal and tender areas before and after treatment.
8) In the case of testing of topical anesthetics or an analgesic drug actions temperature of surface skin of investigated area is monitored and data before and after application of topical anesthesia or an analgesic.
9) The pain thresholds as well as tolerance levels are individual, but suggested actions permit avoidance of temporal skin irritation and skin damage because the pain threshold power level for 980 nm lasing is lower than the damage level.
10) Electrophysiology—Recording Evoked Cortical Potentials: Pulse durations in the range 50-150 ms is selected with power accordingly measured in step 4). The power is adjusted individually in the level between pain threshold and tolerance level. Trigger pulses, synchronized with laser pulses are applied in electroencephalographic recording protocol. The result of recording of A delta fibers (pin prick pain) then the area of hand were stimulated with repetitive laser pulses 5.4 W, 80 ms and inter-stimulus interval 6 sec are shown in FIG. 16A, the location of electrodes for cortical evoked potentials recording are shown in FIG. 16 B.

Example 2

Protocol of Selective Stimulation

Single Warmth Sensation or/and Single Hot Pain, Activation of C Fibers

Warmth sensation Stimulation
The best laser set up parameters for laser at 980 nm:
Pulse duration: 300 ms to 20 s
Beam size: 3-15 mm
Power: 0.3-10 W
1) A collimated beam with diameter 5 mm, power 1 W and pulse duration 5 sec is applied to investigate area of skin to determine the individual sensitivity of C nociceptors. The lasing is stopped when patient or volunteer report feeling either warmth or hot (burning) pain. The duration of applied pulse is measured. The procedure is repeated 2-3 times and after which the obtained pulse duration is used for the investigation of other areas. Every next pulse is applied to new area of skin if pain or other sensation has not disappeared.

2) The expected pulse duration is between 300 ms and 5 sec. A 300 ms power is increased with step of 0.2 W until the appropriate sensation appears. If the sensation doesn't occurred, then pulses with a duration of 5 sec are applied with increasing of power.

3) The inter stimulation time is at least 20 sec or until the pain sensation has disappeared.

4) For measurement of the Wind Up Effect, the area of stimulation is changed for each successive pulse if pulses applied are separated 2-10 sec.

5) Spatial summation curve: Power density of threshold of warmth or pain vs. Size of irradiated spot. Measurement size of irradiated spot is adjusted to 5 mm, 10 mm and 15 mm and actions 1-2 are repeated for each size with the same selected pulse duration.

6) For measurement of temporal summation curve (Power of Pain Thresholds vs. Pulse Duration) the action 2) is repeated with successive pulses. Pulse power is increased in 0.2 W steps. Expected pulse durations 300 ms-20 sec.

7) The time interval between applied laser pulses has to be more than 3-20 sec to avoid an average heating of skin and skin irritation. Exception is Wind Up Effect where indication of state of skin is subjective rating of pain level and monitoring of surface skin temperature.

Figure 14:
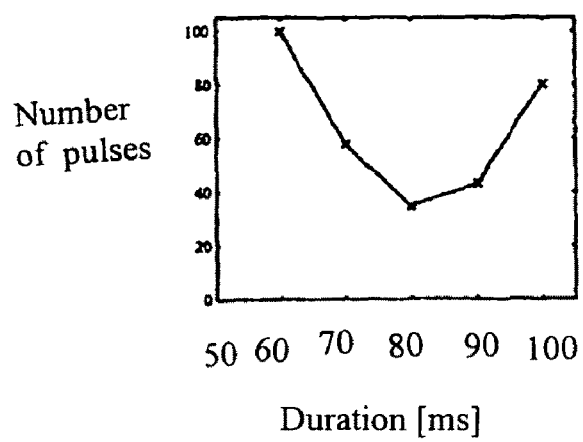
FIG. 14 shows burning pain thresholds with pulse power of 2.5 Watt with variable numbers of pulses and variable pulse durations.
Figure 15A:
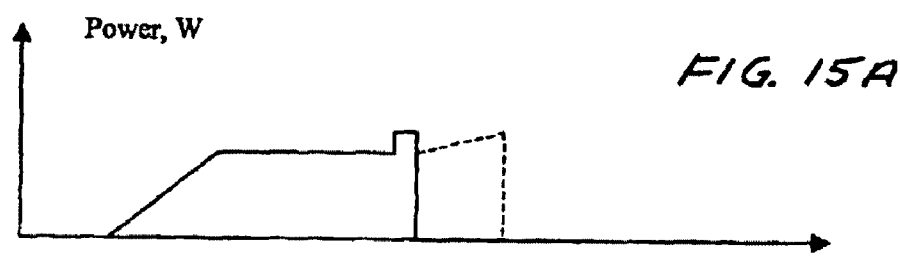
FIGS. 15A and 15B show a preferred tailored pulse for measuring of speed conduction of nerve fibers.
Figure 15B:
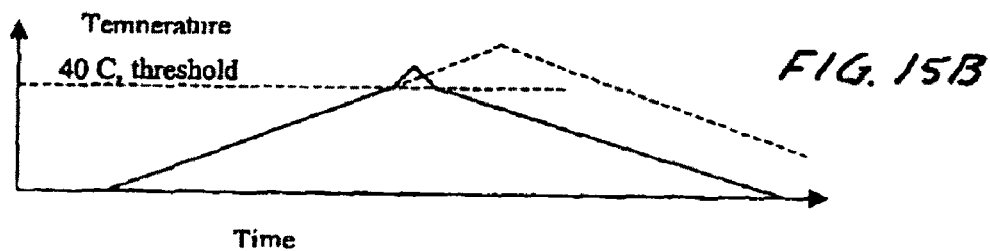

8) For determining of the number of pulses that evoked threshold of hot/burning pain in accumulation of heat the square waved pulses within a range of pulse duration of 10-300 ms and inter-stimulus delay of 0.1-3 sec are applied. The examples of repetitive pulse application for C delta stimulation are shown in FIG. 14.

9) In the case of chronic pain syndromes diagnostics, there are differences between normal skin sensitivity and tender areas for example for fibromyalgia syndrome, the actions 5 and 6 are repeated for normal and tender areas before and after treatment.

10) In the case of testing of topical anesthetics or an analgesic drug actions, temperature of surface skin of investigated area at which pain occurs is monitored and data before and after application of topical anesthesia or a analgesic drug is obtained.

11) The pain thresholds as well as tolerance level are individual but suggested actions permit avoidance of temporal skin irritation and skin damage because the pain threshold level for 980 nm is lower than skin damage level.

12) Electrophysiology—Recording Evoked Cortical Potentials: the pulse duration in the range 300-400 ms (up to 2 sec) is selected. The power may be measured as in step 4. The power is adjusted individually in the level between pain threshold and tolerance level. Trigger pulses, synchronized with laser pulse are applied to electroencephalographic protocols. The jitter from pulse with duration of 300 ms-2 sec could not resolve the time delay between even pulses applied to hand and shoulder for a very tall subject. To solve this problem two optical fiber probes method (see FIG. 5) and signal pulse method (see FIGS. 6A,B and FIGS. 15 A, B) were applied, to measure the time delay between two identically stimulated areas. The time delay was measured by delay time between brief trigger pulses.

Example 3

Application of Protocol Example 2 for Healthy Volunteers

The best laser set up parameters for laser at 980 nm:
Pulse duration: 300 ms to 20 s,
Beam size: 3-15 mm
Power: 1-10 W
Density Energy Range 9-140 mJ/mm$^2$

TABLE 2

Example of threshold Hot Pain and Warmth Stimulations

| Type of sensation | Pulse duration, ms | Area size, mm2 | Power, W | Energy, mJ | Energy Density, mJ/mm2 | Power Density, W/mm2 |
|---|---|---|---|---|---|---|
| warmth | 300 | 38.5 | 4.7 | 1410 | 36.6 | 0.122 |
| warmth | 300 | 176.6 | 5.8 | 1740 | 9.8 | 0.033 |
| warmth | 1300 | 12.7 | 1.1 | 1430 | 112.6 | 0.087 |
| Hot Pain | 300 | 38.5 | 5.8 | 1740 | 45.2 | 0.151 |
| Hot Pain and warmth | 1300 | 19.6 | 2 | 2600 | 132.7 | 0.102 |

Example 4

Group Testing of A Delta Fibers

The following is a description a typical test procedure utilizing the present invention with the application of protocol Example 1 for healthy volunteers and pain patients:

Step 1: Preparing volunteer for test. The volunteers were asked to respond to stimuli after each stimulus was applied, and describing the level and type of evoked sensation, location of sensation, how long the sensation lasts, whether the sensation was single (monomodal) or if more than one sensation were evoked by stimulation.

Step 2: The level of power of laser was adjusted to skin type of volunteer and irradiated spot was selected as close as possible to A-delta receptors.

Collimated beam with diameter 2 mm, within range of power 5.0-10.0 W and pulse duration 100 ms is applied to an investigated area of skin to determine the individual sensitivity and to map the location of A delta nociceptors. The power is increased with step 0.5 W until the first sensation is evoked. After that, the pulse power is fixed and the position of the irradiated spot is scanned (tuned) within an XY frame 5 mm×5 mm to find the location of the nociceptor and pulse power is applied for each new location with spatial steps of around 0.5 mm for fingertips. The inter-stimulus time was at least 20 sec. The first appeared sensation was rated by the volunteer as barely pricking pain without any other sensations of warmth or hot pain.

Step 3

After the location of receptors were determined, the summation curve—Power of Pain Threshold vs. Pulse Duration were measured by the following procedure:

1) Collimated beam was adjusted to 1 mm,
2) Duration of pulse set up to 50 ms and pulse power was increased from 2 W until volunteer reported about first appeared sensation.
3) Afterwards, power was increased until volunteer reported that sensation became clearly painful, but decreasing of power of stimulus on 5-10% leads to the disappearance of pain.

4) Afterward, the power threshold was measured for 50 ms pulse duration was increased by step 50 ms and procedure measurement of threshold was repeated. The increment of power was 0.1 W.

Step 4

The healthy volunteer was tested with pulse durations from 50 ms to 300 ms and beam size of 1 mm. The volunteer reported what around 200-300 ms, he felt on the same level of power firstly warmth and after that pricking pain but for pulses within range 50-150 ms, only single (monomodal) pricking pain was discerned. The sensations were sharp and disappeared in a few seconds after stimulation. The next stimulus was applied not earlier than 20 sec or after the disappearance of painful sensation of previous stimulus.

Step 5

To measure the tolerance level of pain the level of the power was increased more than threshold level with increment of 0.1 W until volunteer reported that his tolerance level of pain had been reached. The procedure of Step 3 was repeated. The volunteer rated his tolerance level as 10 and his threshold level of pain as 1.

Step 6

The thresholds of pin prick pain of healthy volunteers were measured in 20 minutes after topical analgesic (capsaicin) was applied on skin. The Steps 2, 3 and 4 were repeated.

Step 7

To determine a difference in pain threshold and summation curve between healthy volunteer and chronic pain patient the Steps 14 were repeated with patient with chronic hypersensitivity. The result of measurement are shown in Table 3.

Step 8

The level of skin irritation was measured by repetition of stimulation until redness of skin appeared for skin of healthy volunteers for stimulus duration of 150-300 ms and was recalculated for pulse durations of 50 and 100 ms. The Power level evoking skin irritation is shown Table 3.

As it is shown in Table 3, there is enough room to measure dependence of analgesic action between skin damage power level and initial pain threshold of pin prick pain. The shape of summation curve as well as pain thresholds allow to to determine the hypersensitive area of skin of chronic pain patient and test of selective action (A delta vs C fiber) of analgesic as well as diagnosing of that type of fiber is responsible for conducting of pain of patients.

consent and the experiments were approved by the local institutional review board. The hairy skin of left hand was used for both volunteers. In preparing the subjects testing, they were asked to respond orally immediately after they perceived any threshold sensation and/or to interrupt lasing pulse by pressing STOP button. They then described the level and type of evoked sensation, location of sensation, how long the sensation lasted, whether the sensation was single (monomodal) sensation or if there were more than one evoked sensations by a single stimulation. Afterwards, the threshold pulse was applied 3 times to different areas with interval of ~3 min or after the previous sensation (pain) had disappeared. The appearance redness was an indication of skin irritation.

Step 1: To test duration of pulse that evoked threshold warmth sensation only, the output power was set to 1.5 W, beam size adjusted to 5 mm. The pulse was applied to the skin. When the volunteer reported warmth (pain) sensation the lasing was stopped. The measured threshold pulse durations accordingly were 1300 ms for hot pain for the healthy volunteer, 800 ms hot pain for the healthy volunteer affected topical capsaicin (capsaicin decreases the thresholds of warmth sensation and hot/burning pain) and 910 ms hot pain thresholds for the volunteer with the hypersensitivity. The pulse duration for tolerance for hot pain was 2000 ms. Other studies has shown that redness (skin irritation) only occurs when pulse is extended to 3000 ms.

The laser radiation was stopped by volunteer. The volunteer used the other hand to push the "stop lasing" button when he perceived the sensation. When this button was pushed the command "stop lasing" was activated, duration of applied pulse was measured and it was indicated on the screen of PC connected to the device by RS232 interface.

For the double-checking of reflex time of volunteer, a infrared CCD camera (Sony) instead infrared thermal camera (14) FIGS. 1A-1C was applied to monitor the irradiated skin and reflex time. This method allowed to measure the real reflex time without time of delay related of individual reaction of volunteers. For tested volunteers the pulsed durations accordingly were: 1270, 650, 770 ms. This method also permitted the monitoring of the size of irradiated spots directly by infra red lasing as opposed to use the aiming beam. However, there was not found any differences between the diameter aiming beam and the diameter acting infra red lasing beam of irradiated spot. Accuracy of beam size measurement was +/−0.50 microns.

Step 2: To measure the speed conductivity of C fiber alternatively of two probe method power which evoked hot pain sensation for pulse a duration of 300 ms was determined. This pulse duration is short enough to use it for measurement of speed conductivity by electroencephalographic recording of cortical evoked potentials. The output power was set up 1 W,

TABLE 3

| Pulse Duration, (ms) | Power of Pain Thresholds of Healthy Volunteer, (W) | Power of Pain Tolerance of Healthy Volunteer, (W) | Power of Skin Irritation, (W) | Power of Pain Thresholds of Healthy Volunteer (Capsaicin), (W) | Power of Pain Threshold of Chronic Pain Patient with Hypersensitivity, (W) |
|---|---|---|---|---|---|
| 50 | 9.5 | 11.9 | 16.6 | 14.8 | 7 |
| 100 | 4.5 | 5.6 | 7.9 | 7.0 | 3.5 |
| 150 | 3.2 | 4 | 5.6 | 5 | 2.5 |
| 200 | 2.8 | 3.5 | 4.8 | 4.3 | 2.2 |
| 300 | 2.5 | 3.1 | 4.4 | 3.9 | 2.2 |

Example 5

Stimulation of C Fibers

Comparison of Chronic Pain Patient to Healthy Volunteer

Subjects: A chronic pain patient with hypersensitivity and a healthy volunteer were tested. Both subjects gave informed spot size 7 mm with an increment of power was selected 0.1 W. The volunteer was asked to report the threshold of pain, skin sensation tolerance.

Example 6

Activation of Heat Sensitive Ion Channels of Vanilloid Receptors

For this experiment membrane patches are derived from transfected mammalian cells expressing VR1. Experiments are carried out with human embryonic kidney (HEK293) cells expressing the rat VR1 cDNA (Caterina M J, Schumacher M A, Tominaga M, Rosen T A, Levine J D, Julius D. The capsaicin receptor: a heat-activated ion channel in the pain pathway. Nature 1997; 389:816-824.; Tominaga M, Caterina M J, Malmberg A B, Rosen T A, Gilbert H, Skinner K, Raumann B E, Basbaum A I, Julius D. The cloned capsaicin receptor integrates multiple pain-producing stimuli. Neuron 1998; 21:531-543) Cells are plated on glass cover slips for whole-cell patch-clamp recording procedures or for obtaining excised membrane patches, as previously described by the Chuang (Chuang, H., Prescott, E. D., Kong, H., Shields, S., Jordt, S. E., Basbaum, A. I., Chao, M. V., and Julius, D. (2001) Bradykinin and nerve growth factor release the capsaicin receptor from PtdIns $(4,5)P_2$-mediated inhibition. Nature 411: 957-962). Once high resistance seals to the membrane and stable recordings had been obtained, the laser was positioned close to the cell or excised patch so as to deliver a brief (10-100 mS) pulse. Laser-evoked membrane currents were recorded and analyzed with standard packages (PClamp, Axon Inst.). Current-voltage traces and blockade by VR1 antagonists (capsezapine and ruthenium red) were used to assess the identity of the evoked currents. Negative controls to assess background currents were performed with HEK293 cells expressing other, non-heat-sensitive ion channels.

Figure 17A:
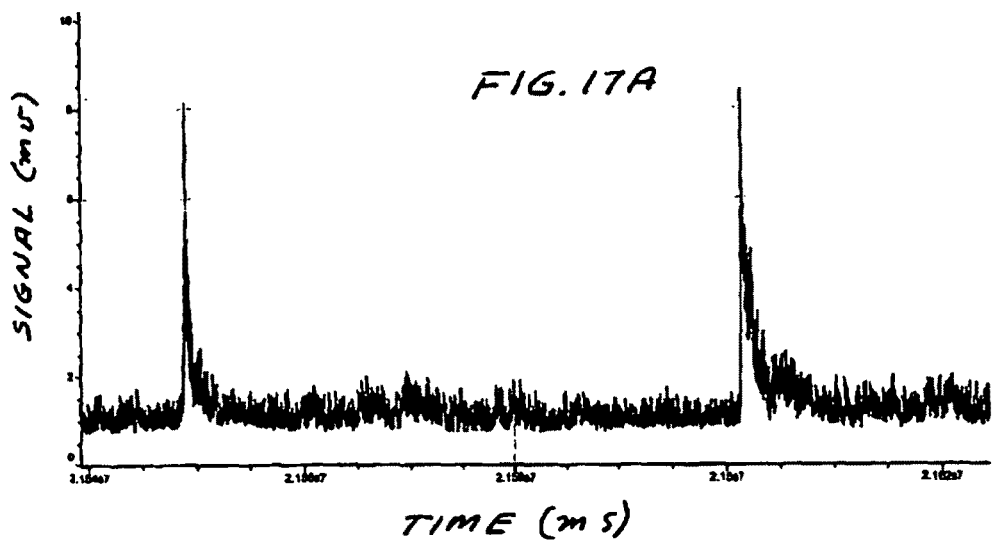
FIGS. 17A and 17B show results of ion channel experiments.
Figure 17B:
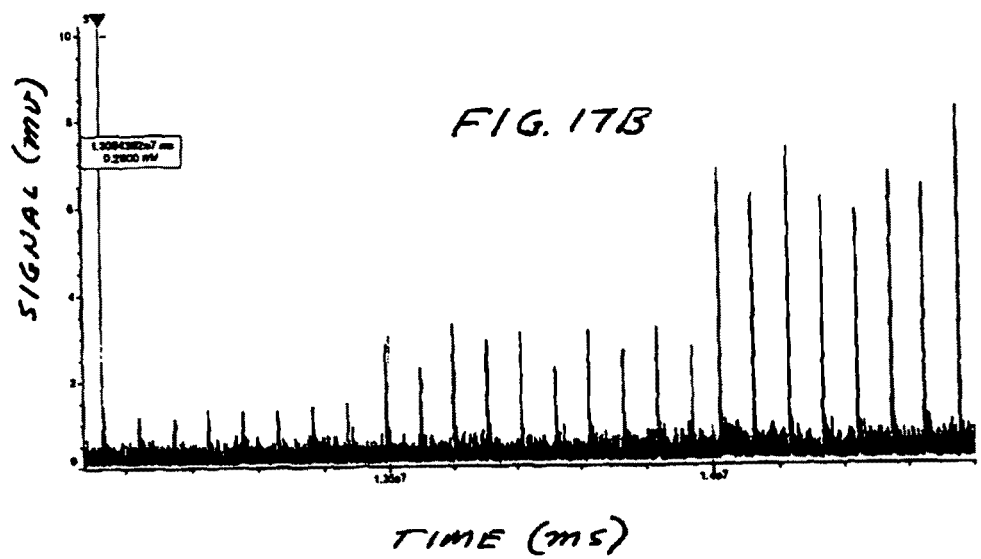

The free 100/125 microns tip of the optical fiber of laser stimulator with an output power of 5 W was used. The distance between membrane patches fixed on pipette and tip of optical fiber was 50 microns. Three pulse powers were applied: 3 W, 4 W, 5 W. Each power set was applied with inter stimulus delay of 10 sec and a pulse duration of 50 ms. The two sets of two different membrane patches were provided. The results are shown in FIGS. 17 A and 17 B. The standard deviation of laser induced amplitude of ion channel current was less than 12% for each set of output power. There was not observed any post activation effects. The effective peak temperature of activation was determined by the following procedure: A part of membrane patches were heated until a maximum ion channel current was achieved and this procedure was repeated. At room temperature membrane patches were activated by capsaicin. The laser stimulation was used to control when (and what percentage ~100%) ion channels are opened. Laser induced ion current decreased and DC current increase until the laser induced current decreased to 0. For kinetic protocols pulse durations from 20 to 50 milliseconds with 4 W out put power were applied.

The stimulation of C and A-delta terminals is a result of activation of heat sensitive ion channels and depolarization on cell membranes of the terminals. The research in this direction may be determined by what vanilloid receptors (VR1 or VRL1) are responsive for heat activation of C and A delta fibers. These receptors have different threshold temperatures and could be correspondingly linked to C or A-delta terminals. The monitoring of their thresholds and kinetics permits the diagnosing of peripheral pain syndromes and evaluation of analgesic drug action on C and A delta terminals.

Example 7

Stimulation of C Fibers of Rats and Influence of Drug on Pain Thresholds

Animals: Male Sprague-Dawley rats (258±20 g, Charles River Laboratories) were housed in a 12/12-hour light/dark environment and provided food and water ad libitum (n=24). Effort was made to minimize discomfort and reduce the number of animals used.

Step 1

Rats were lightly anesthetized with urethane (1000 mg/kg ip) and placed with minimal restraint on a heating pad to maintain their body temperature at 37° C. Rats were slightly restrained in plastic cone, head and neck of rat was free of restrain.

Step 2

Laser pulses beam 5 mm spot diameter, power 0.8 W power and 30 sec pulse duration were applied to the ears and nostrils of rats. The lasing was terminated immediately upon withdrawal of ear or nose to prevent tissue damage.

Step 3

Step 2 was repeated for left and right ears and left and right nostrils of rats. The stimulation site was changed after each long pulse allowing at least 2 minutes in between 2 stimuli on the same ear or nostril. The testing sessions were videotaped for precise measurement of response latencies.

Step 4

One of three drugs, Capsaicin, Morphine or Dimethyl Sulfoxide (DMSO) were applied for each rat. Thereafter, 5 mm, 0.8 W, 30 sec laser pulses were applied and response latencies were measured.

Description of applied drug: Capsaicin (10 mM, Sigma-Aldrich Co., St Louis, Mo., USA) was dissolved in 50% ethanol in $H_2O$ and applied to rats in group 1. Rats in group 2 received DMSO (dimethylsulfoxide, Sigma-Aldrich Co., St Louis, Mo., USA). Capsaicin and DMSO were applied to the ear with cotton tipped applicators. Rats in group 3 received an intramuscular injection of morphine (1 mg/kg, Lylly). Response latencies were re-tested 20 minutes after the drugs had been administered. Measured latencies were analyzed using NONMEM® (GloboMax LLC, Hanover, Md.).

Figures 18, 19:
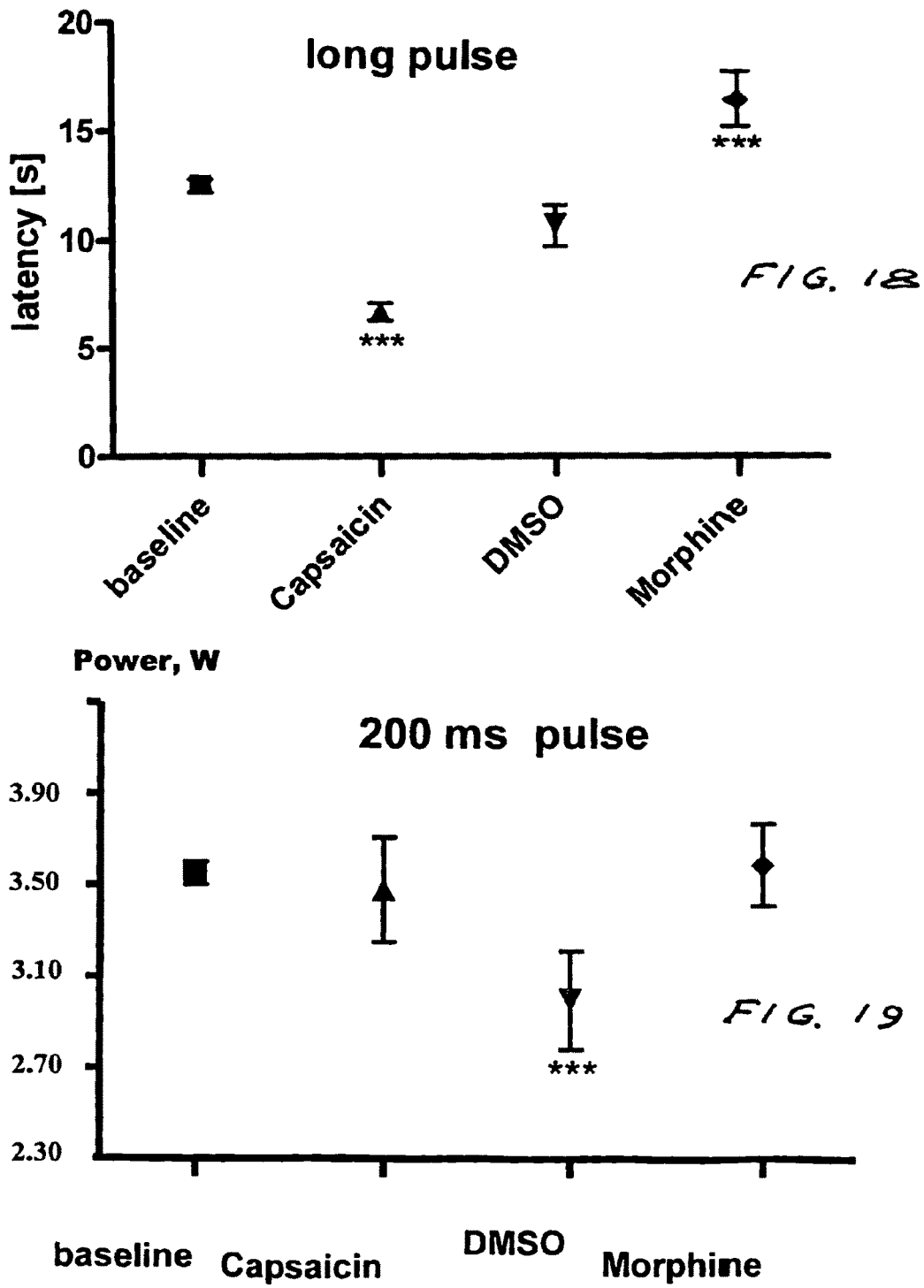
FIG. 18 show results of drug action on C fiber stimulation in rats.
FIG. 19 show results of drug action on A-delta fiber stimulation in rats.

6 rats were tested with each drug. Results of behavioural test of rats of C fibers stimulation for each drug are shown in FIG. 18.

Example 8

Stimulation of A Delta Fibers of Rats and Influence of Drug on Pain Thresholds

Animals: Male Sprague-Dawley rats (258±20 g, Charles River Laboratories) were housed in a 12/12-hour light/dark environment and provided food and water ad libitum (n=24). Effort was made to minimize discomfort and reduce the number of animals used.

Step 1

Rats were lightly anesthetized with urethane (1000 mg/kg ip) and placed with minimal restraint on a heating pad to maintain their body temperature at 37° C. Rats were slightly restrained in plastic cones, head and neck of rat were free of restraint Step 2

Laser beam pulses (2 mm spot diameter, duration 200 ms) were applied to the ears and nostrils of rats. Stimulation was started with output power well below the typical threshold of 0.5 W. After each short pulse the testing sites were alternated as well allowing at least 45 seconds in between 2 stimuli applied to the same ear. Step of increasing of power was 0.1 W The testing sessions were videotaped for precise measurement of latency time.

Step 3

Step 2 was repeated for left and right ears and left and right nostrils of rats. The stimulation site was slightly changed after each brief pulse allowing at least 45 sec in between 2 stimuli on the same ear or nostril. The testing sessions were videotaped for precise measurement of time.

Step 4

One of tree drugs, Capsaicin, Morphine or Dimethyl Sulfoxide (DMSO) were applied for each rat. Thereafter, 5 mm, 0.8 W, 30 sec laser pulses were applied and response latencies were measured.

Description of applied drug: Capsaicin (10 mM, Sigma-Aldrich Co., St Louis, Mo., USA) was dissolved in 50% ethanol in $H_2O$ and applied to rats in group 1. Rats in group 2 received DMSO (dimethylsulfoxide, Sigma-Aldrich Co., St Louis, Mo., USA). Capsaicin and DMSO were applied to the ear with cotton tipped applicators. Rats in group 3 received an intramuscular injection of morphine (1 mg/kg, Lylly). Response latencies were re-tested 20 minutes after the drugs had been administered. Measured latencies were analyzed using NONMEM® (GloboMax LLC, Hanover, Md.

Six rats were tested with each drug. Results of behavioural test of rats of A delta fibers stimulation for each drug are sown in FIG. 19.

Recent Research

Examples 9 through 14 provided below describe the results of recent research by Applicant in furtherance of the present invention.

Example 9

Activation of TRPV1 Positive and TRPV2 Positive Cells

TRPV1 Infected HEK293 Cells:

HEK293 cells were cultured in DMEM/F12 with 10% FBS (fetal bovine serum) and transfected using Lipofectamine Superfect or Fugene 6 according to manufacturers' protocols. Cells were transfected with 400 ng plasmid DNA encoding rat VR1, with or without 400 ng human $BK_2$ receptor complementary DNA. To identify transfected cells, an enhanced green fluorescence protein reporter plasmid was also transfected at one-tenth the concentration of receptor cDNAs. Cells were plated onto coverslips 1-3 days before recording and examined 4-7 days post-transfection. Voltage-clamp experiments were performed at −60 mV holding potential with 320 ms voltage ramp from −120 mV to +80 mV at 1 Hz. Data was acquired using pClamp (Axon Instruments) or Pulse-Pulsefit (HEKA GmBH) software. Recordings were filtered at 5 kHz and sampled at 1 kHz. Standard bath solution for patch-clamp experiments contained 10 mM Tris/HCl, 1 mM EGTA, 1 mM $MgCl_2$ and 150 mM CsCl at pH 7.4. The pH 6.4 solution contained 20 mM citric acid and 1 mM $MgCl_2$, titrated with CsOH to pH 6.4 and supplemented with CsCl to make the final $Cs^+$ concentration 150 mM. For excised patch experiments, standard bath solution was used in both the pipette and perfusion solution. No ATP was added to the solutions. Diameters of patch pipettes were 12-15 μm for HEK293 cells and recorded. The bath temperature was monitored with probes (Warner Instruments).

TRPV1 and TRPV2 DRG Cells

Rats were anesthetized with halothane. Following decapitation, the spinal cord was rapidly removed, and the dorsal root ganglia were dissected free. Dissected ganglia were placed in a heated bath (35° C. for 70 min) containing dispase II and collagenase (2 mg/ml; Sigma type 1). Following wash and trituration, recovered cells were plated on 10 polylysine coated, 35 mm Petri dishes. Cells were bathed continuously in a rat Tyrode's solution containing (mM): 140 NaCl, 4 KCl, 2 $MgCl_2$, 2 $CaCl_2$, 10 glucose, and 10 HEPES, pH adjusted to 7.4 with NaOH. Only one cell was used from each dish. Bath temperature was maintained at 32° C. by a feedback-controlled bath heater (TCbip; Cell Microsystems).

Whole Cell Patch Recording

Electrodes were prepared (2-4 MΩ) from glass pipettes using a Brown and Flaming type horizontal puller (Sutter model P87). Whole cell recordings were made with an Axopatch 200B (Axon Instruments). Stimuli were controlled and digital records captured with pClamp 8.2 software and Digidata 1322A A/D converter (Axon Instruments). Series resistance ($R_s$) was compensated 40-60% with Axopatch 200B compensation circuitry. Whole cell resistance and capacitance was determined by Clampex 8.2 software utility. A liquid junction potential of approximately 4 mV was not corrected.

Cell Classification Protocols

Recordings were made from cells with diameters between 25 and 45 μm. Cells were classified as type 2 or 4 according to patterns of voltage-activated currents (current signatures) that were revealed by three-classification protocols. Cells classified in this manner have consistent anatomic, pharmacologic and histo-chemical properties. Cell types 2 and 4 have been identified as putative C and A delta skin heat nociceptors that express TRPV1 (type 2) or TRPV2 (type 4)

Cell Stimulation:

Lass 10 M investigational diode laser (Lasmed LLC) was used in all studies. The Lass 10 M operates at a wavelength of 980 nm, maximum outpower of 15 W. For these studies pulse durations varied from 10-50 ms. For both patch clamp experiments and compound action potential recordings, the radiation was delivered by standard optical fiber: NA 0.22 core/cladding 0.100/0.140 mm. The diameter of laser beam at cell and nerve was varied from ~0.1 mm to 0.5 mm. The calibration of laser power was performed by Ophir Nova power/energy meter (Ophir Inc.). Three levels of power: 3, 4 and 5 W with pulse duration 50 ms and pulse interval 10 s were used to stimulate selected TRPV1-expressing HEK293 cells. DRG cells TRPV1 positive cells (Type 2) and TRPV2 positive cells (Type 4) were irradiated with a pulse duration of 20 ms and pulse interval $\geq$10 s. The fiber was positioned 112 um from the targeted cell at an angle of 60 degrees. The power of laser pulses was gradually increased from 0.300 W to 4.5 W with 0.5 W steps to form saturation curves.

Ten excised patches of HEK293 cells were tested (TRPV1 expressing, n=9; control, n=1). The laser stimuli (3 W, 4 W, and 5 W 50 ms pulse duration) produced consistent activation of TRPV1 with relatively low variation between tests normalized STD of laser evoked current (10 stimuli with the same power) ranged from 12-36%. Background noise remained constant throughout the study (<30 pA). Representative HEK cell reactivity of TRPV1 is presented in FIG. 20 A.

Over the range of stimulation, laser-evoked current responses were highly reproducible and stable over the time-frame of the experiments. The results confirmed our preliminary data that over test periods of up to 2 hours, there was no significant cell degradation attributable to laser irradiation. Similar properties were observed in DRG neurons. High reproducibility indicates and absence of time dependent sensitization or desensitization of TRPV1 currents in HEK293 cells with repetition rate 0.1 pulse/s.

Properties of proteins expressed in neurons may differ from those artificially expressed in host cell systems (e.g. HEK293). Using the diode laser, we examined TRP protein reactivity in distinct classes of hairy skin nociceptors, which differentially express either TRPV1 (type 2) or TRPV2 (type 4). These nociceptor classes represent capsaicin sensitive (type 2) and insensitive (type 4) neurons which are both heat reactive. Fluid superfusion thresholds are 45 and 52° C., respectively. These neurons may represent classic C-PMN and Aδ-MH I class nociceptors that have been identified and characterized in vivo as afferents mediating slow burning and fast pricking pain. Laser activation produced inward currents of exceptionally fast kinetics relative to those normally observed with other heating methods FIG. 20 B.

Figure 20:
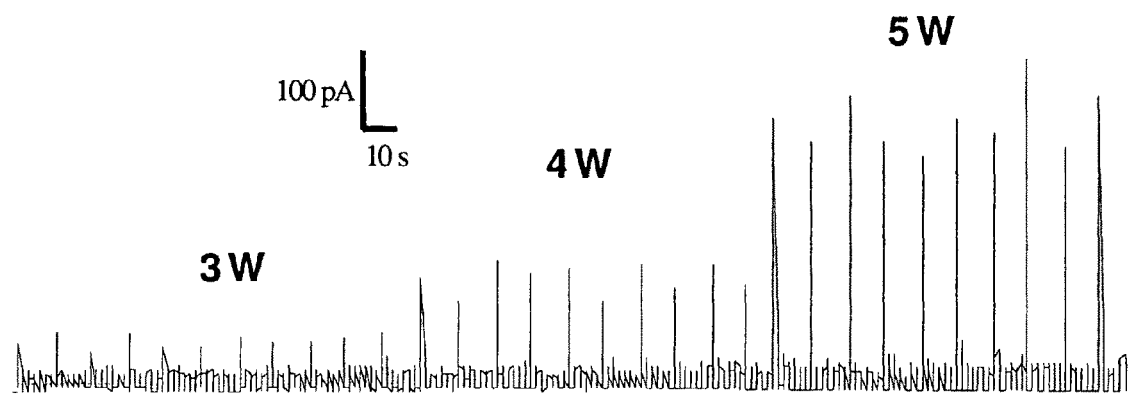
FIG. 20 D shows reduced currents evoked by 980 nm stimuli as a result of applications of capsazepine.
Figure 20:
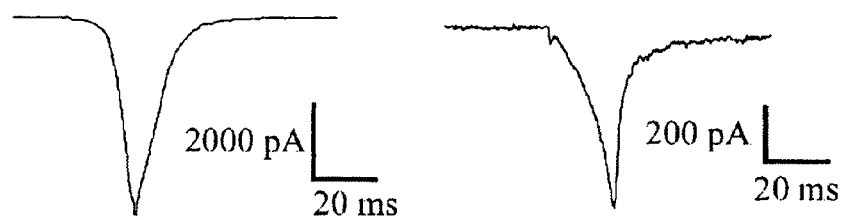
Figure 20:
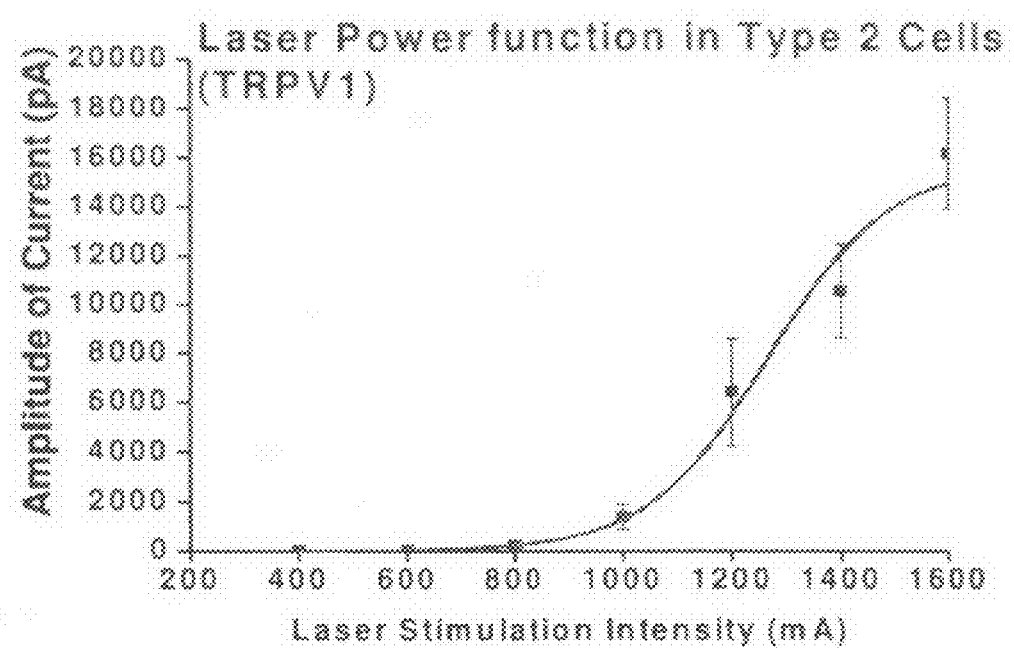
Figure 20:
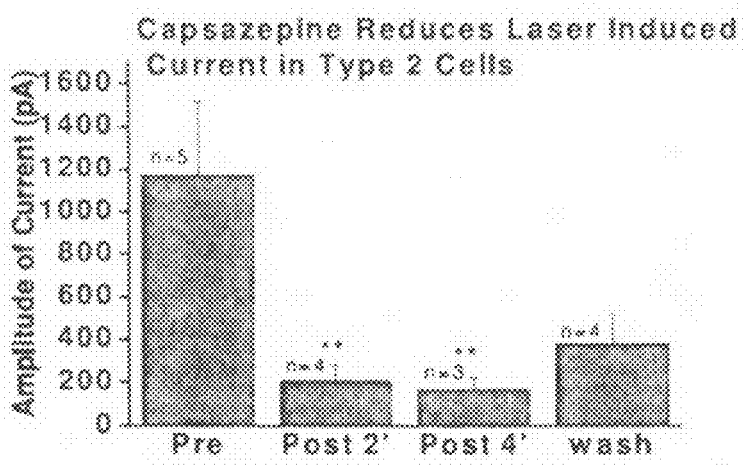

Consistent with the mediation of currents by TRPV1, application of the selective TRPV1 antagonist capsazepine, dramatically reduced currents evoked by 980 nm stimuli FIG. 20 D. Capsazepine (10 uM) was applied by close superfusion (two minute application) following evocation of a baseline response. All cells were stimulated with identical laser pulses: 20 ms and 2.41 W (1200 mA).

The full reactivity of TRP proteins are difficult to examine due to limitations imposed by fluid heating methods. Fluid heating is difficult to control, and may degrade membrane proteins over long exposure times required to maximize activation. We were able to drive TRPV1 currents through their full reactive range with little difficulty using 980 nm stimuli FIG. 20 C. The threshold of laser stimulation was ~400 mA (~1.0 W). The saturation current/power was 1400 mA (~2.93 W). The estimated corresponding temperature threshold, extrapolated from a thermal calibration procedure[30] was approximated at ~55° C. These estimated threshold temperatures are substantially higher than the thresholds (42° C.) of TRPV1-infected HEK293 and TRPV1 positive DRG cells (46° C.), as determined by stimulation with heated fluids 5-20 sec. Our experiments in humans have shown that short diode laser pulses produce corresponding increases in thresholds of human pain report (57° C. and 75° C. for 300 and 50 ms pulses respectively.

Conclusions from Example 9

These experiments in this Example 9 shows that laser irradiation at 980 nm wavelength delivered by optical fiber with 100 micron core is a selective, reproducible and noninvasive stimulus for activation of TRPV1 and TRPV2 positive cells. The applicable parameters of laser irradiation and laser induced temperature in cell experiments are specified for activation of C (TRPV1) and A delta (TRPV2) nociceptors in rodents and humans.

Example 10

Deactivation of TRPV1 Positive Cells

Heat Desensitization

Heat may cause TRPV1 to desensitize as capsaicin does. The desensitization of TRPV1 has therapeutic potential. Topical capsaicin and other naturally occurring pungent molecules have long been used as analgesics to treat a variety of chronic pain conditions. The analgesic effects of these compounds have been attributed to their ability to desensitize nociceptors into a lasting refractory state. Development of nonirritant TRPV1 agonists, i.e. ligands that do not evoke action potentials that lead to pain but desensitize TRPV1, has been actively pursued as alternatives to TRPV1 antagonists for pain relief. The desensitization of TRPV1 has been studied mostly with capsaicin as agonists. The experiments require repeated applications of stimulus. This is difficult with traditional heating methods such as exchange of entire bath solutions. They are often slow and destructive to patch seals, making it difficult to carry out the measurements over long periods. As a result, little is known about the nature of state of the channel following activation by heat.

Heat (45 C) was applied for prolonged period until the currents become inactivated 1-10 s. The temperature of cell located at the bottom of petri dish was controlled by temperature feedback (sensor 16, in FIG. 3). The short pulse stimuli of 50 ms were applied in 5-10 min to detect the recovery of the currents from desensitization.

HEK 293 cells were prepared and inward current recording was performed as described in Example 9 current application. Patch electrodes are pulled from borosilicate glass (World Precision Instruments, Inc.), coated with Sylgard (Dow-Corning, Midland, Mich.), then fire-polished to a tip resistance ranging typically 1-2 MΩ for whole-cell recordings. Currents are recorded with a patch-clamp amplifier (Axopatch 200B; Axon Instruments), filtered at 1 kHz and sampled at 5 kHz. Data are digitized directly onto the computer hard disk using a LabView data acquisition system (National Instrument). For whole-cell recordings from HEK293 cells, the standard bath solution contains (mM): 150 NaCl, 10 EGTA, 10 HEPES, pH 7.4 (adjusted with NaOH). No $Ca^{2+}$ is included to avoid desensitization. The internal pipette solution contains (in mM) 150 KCl, 5 EGTA, 10 HEPES, pH 7.4 (adjusted with KOH). The perfusion solutions are the same as the bath solutions except for appropriate agonist. Perfusate is driven by an ALA BPS4 perfusion system (ALA Scientific Instruments). Experiments other than temperature related are conducted at room temperature (25° C.).

Figure 23:
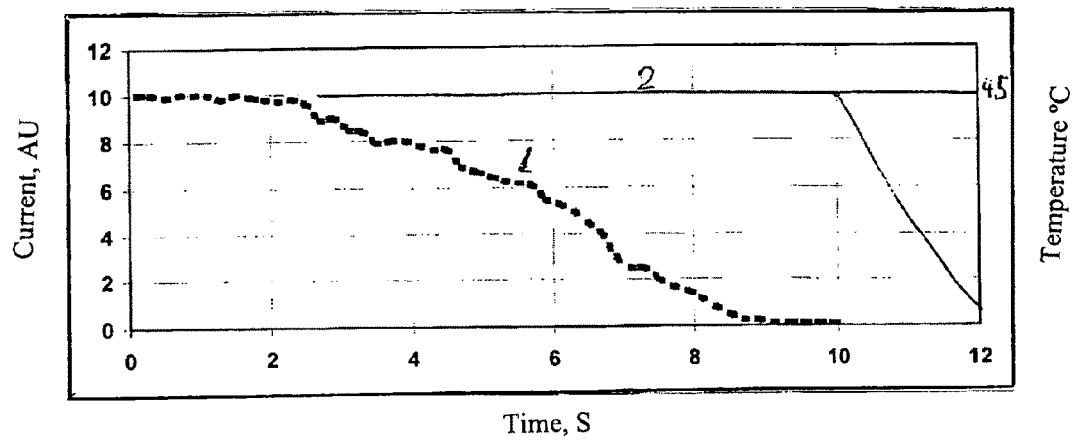
FIG. 23A shows an inward current (2) of trpv1 positive cell under application of laser induced constant temperature (1) of 45° C. during 10 sec.
FIG. 23B shows an inward current of trpv1 positive cell then laser pulses with pulse duration 50 ms and interval 200 ms that keep average temperature on cell 46° C. are applied to cell during 10 sec.
Figure 23:
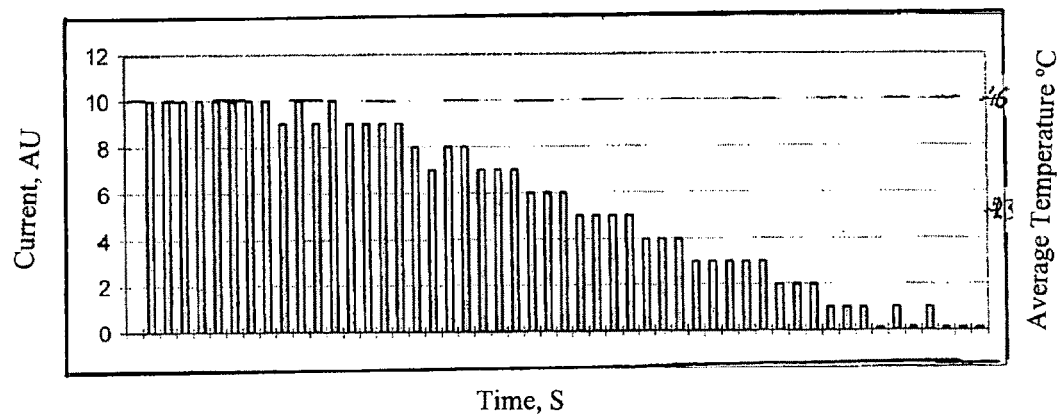

Increase of duration of laser pulse that maintain cell temperature at 45 C up to 2 s and more leads to a decrease of inward current and a deactivation of tested cells FIG. 23 A. The brief laser stimuli of 50 ms that usually evoked substantial inward current FIG. 20 A that were applied in 1-5 min after the prolong pulse was applied did not evoked any cell response (inward current). The application sequence of pulses FIG. 23 B that maintain average cell temperature at 46 C leads the same effect of cell deactivation and desensitization as prolong pulses. The results of deactivation and desensitization are presented in FIG. 23.

Conclusions from Example 10

This example 10 shows that laser irradiation permits noninvasive deactivation of TRPV1 positive cell, with heat playing an important role. The mechanism of deactivation could be close to the mechanism of deactivation produced by Capasaicin. This mechanism can permit the development of pain relief and local anesthesia techniques for human and animal application.

Example 11

Activation of Heat Sensitive Single Cell and Groups of Cells In Vivo

Electrophysiological Experiments

Electrophysiological experiments were performed with electrical and laser stimulation. The rats were prepared as previously described. Rats (250-300 g) were anesthetized with sodium pentobarbital. At the end of the experiment, the rat was euthanized by pentobarbital overdose. Recordings of compound action potentials were made from the saphenous nerve. Bipolar stimulating electrodes were placed under the nerve distal to the recording site. Laser stimuli were applied in the area between the bipolar-electrode pair. The nerve was crushed proximally to the recording site to prevent flexor reflexes during electrical stimulation of the nerve. Mineral oil was used for electrical isolation. Conduction velocities of activated fibers were calculated by dividing the distance between the stimulating and recording electrodes (~30 mm) by the latency of the electrically and laser evoked action potentials. Fibers that conducted slower than 2 m/s were classified as C-fibers.

The Lass 10 M investigational diode laser (available from Lasmed LLC with offices in Mountain View, Calif.) was used in all studies. The Lass 10 M operates at a wavelength of 980 nm, maximum outpower of 20 W. For these studies pulse durations varied from 10-200 ms. For compound action potential recordings, the radiation was delivered by standard optical fiber: NA 0.22 core/cladding 0.100/0.140 mm. The diameter of laser beam at cell and nerve was varied from ~0.1 mm to 0.5 mm. The calibration of laser power was performed by Ophir Nova power/energy meter (Ophir Inc.).

Figure 21A:
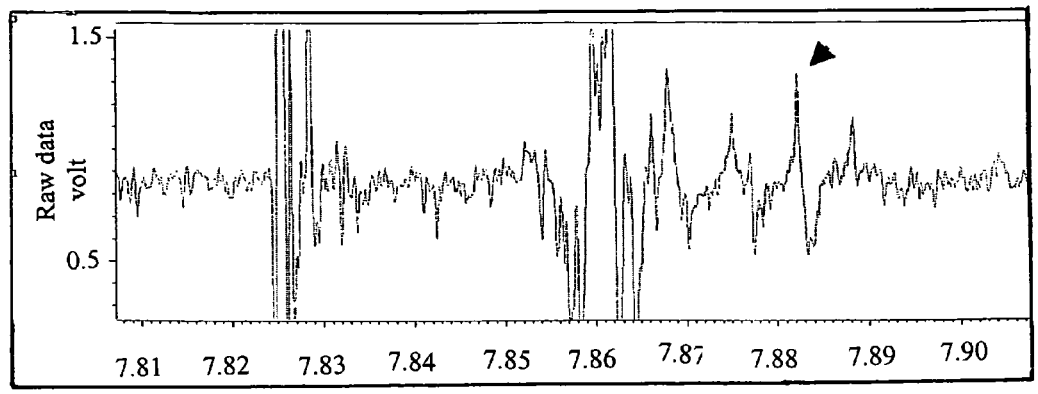
FIG. 21A shows the recorded compound action potential of the trunk of a saphenous nerve evoked by electrical stimulation (0.25 ms).
Figure 21B:
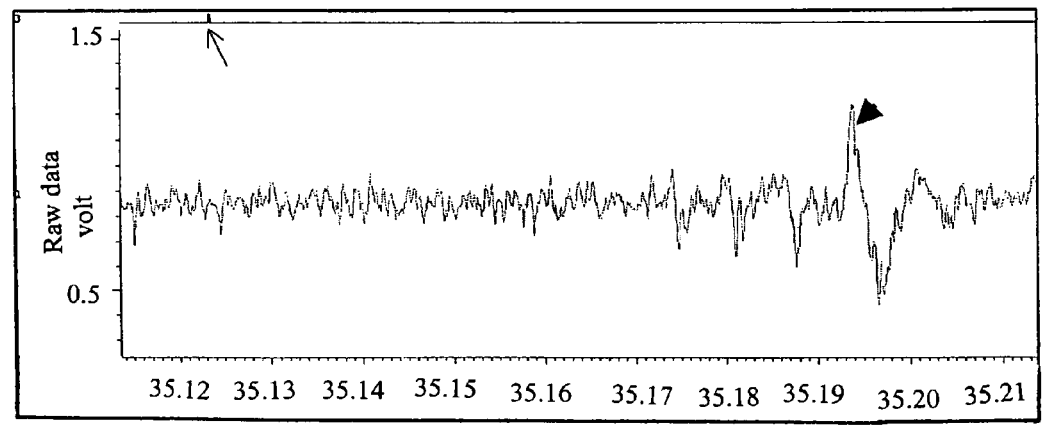
FIG. 21B shows a compound action potential of the trunk of the saphenous nerve evoked by diode laser stimulation (20 ms). Note the reduction in artifact and neural components with laser stimulation. Thick arrows indicate the heat sensitive C fiber components. Thin arrows indicate diode laser stimulus onset.

Electrical stimulation of the saphenous nerve activated a wide range of neural activity that included contributions from axons of A beta, A☐ and C fiber groups FIG. 21A. A substantial electrical artifact was also present. In contrast, laser stimulation activated only C fiber axons FIG. 21B. The conduction velocity of electrically activated C axons was ~0.46 m/s (late component of FIG. 21A; mean latency 65 ms). The conduction velocity of laser activated axons was about 0.42 m/s (mean latency 70 ms). These latencies are consistent with C fibers. The activation by 980 nm irradiation was much better isolated from other nerve activity.

Conclusions from Example 11

This Example 11 supports Applicant's conclusion that the laser irradiation may directly or via skin activate single nerve fibers or groups of nerve fibers. The experiment also suggests that the active mechanism is primarily heat activation of heat sensitive ion channels located in nerve cell membranes.

Example 12

Application of Pin Prick vs. Burning Pain Stimulation with FMRI Registration

Pin Prick Pain

Diode laser pulses from 25 to 200 ms were applied to area of skin with diameter of 1 mm were delivered via optical fiber with core diameter of 100 microns and collimated to skin of right hand of 6 healthy volunteers to evoke pin prick pain and activate A fibers.

Burning Pain

Diode laser pulses from 0.5 to 2.0 s were applied to area of skin with diameter of 5 mm were delivered via optical fiber with core diameter of 100 microns and collimated to skin of right hand of 6 healthy volunteers to evoke burning pain and activate C fibers. The length of optical fiber was 15 m the repetition rate for both type of stimulation was varied from 0.05 pulse/s to 0.5 pulse/s.

Conclusions from Example 12

Figure 22:
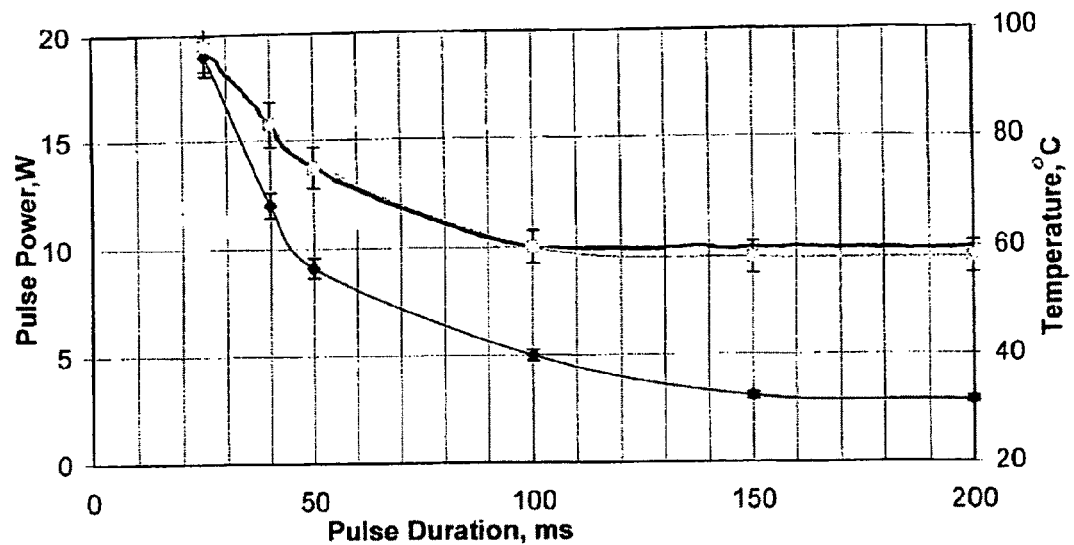
FIG. 22 A shows a dependence of total laser induced temperature (1) and laser power (2) that evoked threshold (0-10 VAS pain Intensity Rating on a 1-100 scale) pin prick pain on pulse duration of 25-200 ms of laser stimulation. Heat rate: 300-3000 C/sec.
Figure 22:
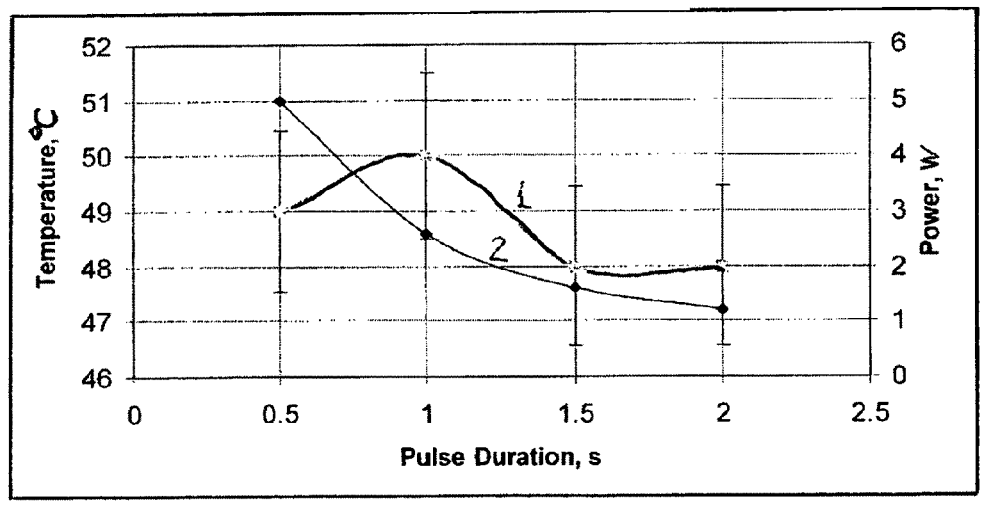

The results of these tests are shown in FIG. 22. The selected stimuli parameters that maintain maximum temperature of 75 C at 50 ms pulse (pin prick) and 49 C at 1500 s pulse (burning) were applied to pre-tested volunteers as it described above. These stimuli provoke reproducible response among volunteers before, during FMRI test and after with 10 to 20 of VAS pain Intensity Rating on a 1-100 scale. The results of the selected stimuli action are presented in FIG. 24, repetition rate 0.1 pulse/s.

Example 13

Local Laser Induced Anesthesia and Pain Management Based on Deactivation of TRPV1 Positive Nociceptors Laser Induced Analgesia This example was performed to determine if the diode laser could be used to produce temporary anesthesia in skin tissue. Diode laser stimuli parameters below pain threshold for pain pin prick stimulation were established. These parameters were 50 ms pulses to maintain 70 C were selected for test. Laser pulses were delivered to the right hand of volunteers as described in Example 12. The site of irradiation was slightly shifted after each stimulation. The response was with 5-10 of VAS pain Intensity Rating on a 1-100 scale. This intensity of response is usually reported as non painful pricking sensation. These stimuli were applied with repetition rate of 4 pulse/s over area of 25 mm diameter.

Before and After Laser Induced Anesthesia

Before

Before applying the above laser induced anesthesia six healthy volunteers were tested with a sequence 40 pulses (with 50 ms duration) to maintain a temperature of about 75 C. This evoked painful pin pricking pain. The volunteers were then tested with single 1500 ms pulses. This evoked burning pain.

Soon After

Five minutes after applying the above laser induced anesthesia the six healthy volunteers were tested with the same sequence 40 pulses (with 50 ms duration) to maintain a temperature of about 75 C. This did not evoked painful pin pricking pain. The volunteers were then tested with single 1500 ms pulses. This also did not evoked burning pain.

Long After

Tests were also performed on the volunteers to determine if the laser induced anesthesia effects were long lasting. These tests confirmed that after periods substantially longer than about 5 minutes, the skin tissue had returned to normal with no lasting anesthesia effects.

Conclusions of Example 13

FIG. 24 shows a result of application laser of single and repetitive laser stimulation that evoked
1. reproducible stimulation of:
   a) pin prick pain and A nerve fiber or group of fibers activation: pulse duration 50 ms, with temperature 74-75° C. repetition rate 0.1 pulse/s,
   b) burning pain and C nerve fiber or group of fibers activation: pulse duration 1500 ms, repetition rate 0.1 pulse/s
2. decreased with time response (pain inhibition) to laser stimulation of 100 laser pulses with duration 50 ms, repetition rate 4 pulse/s and temperature 75° C. The laser stimuli of 50 ms with 75° C. evoked temperature as well as 1500 ms with 49° C. evoked temperature did not evoked pain than they applied after the sequence of 100 pulses.

These results suggest that at least temporary anesthesia to the skin from pin pricking and burning pain can be produced with diode laser radiation. The temporary pain relief by blocking of C fibers may decrease the level of inflammation and cause permanent healing and pain relief.

Example 14

Application of Pin Prick vs. Burning Pain Stimulation to Monitor Anesthesia Monitoring Anesthesia In this example the diode laser was tested to determine if the diode laser would be a practical technique for monitoring anesthesia induced by standard prior art techniques. Anesthesia intervention using opioid was applied to test volunteers. Then laser stimuli as described in Example 12 that evoked reproducible pin prick and/or burning pain were applied. The parameters of stimuli are shown in FIG. 25. These stimuli are at levels slightly higher compared clear distinguished pain thresholds.

Conclusions from Example 14

FIG. 25 shows results of laser stimulation of pin prick pain (A fibers) 50 ms pulses and burning pain (C fibers) 1500 ms pulses of humans before and after anesthesia intervention with opioid. The sensitivity to 50 ms pulses that produced heating to 75° C. after intervention slightly decreased but pulses of 1500 ms that evoked 50° C. after intervention became non painful. These parameters used in this example are above the pain threshold but below the skin tissue damage threshold. The ratio of response in between 50 ms and 1500 ms, before after and during anesthesia, shows that the diode laser can be used to monitor state of human sensitivity to pain while subject to standard prior art anesthesia techniques.

Comparison Of In Vivo and In Vitro Pain Results

This idea was experimentally tested when the adequate laser heat stimuli were applied in vivo to the skin of volunteer and in vitro using of the somata of dorsal root ganglion (DRG) neurons. (prototype paper). The absorption of human and animal skin of near infrared light in the interval of 900-1600 nm is mostly determined by water absorption. Thus, the location of investigated cells from DRG as well as cell membrane patches in water solution in depth close to the depths location of nociceptor terminals in the skin ~300-600 microns can allow directly experimental comparison of activation by the same stimulation parameters of laser stimuli in vitro and in vivo.

General Algorithms

The following are examples of control algorithms that are useful in setting up the laser and optics for practicing the present invention:

1) Standard square wave laser pulses:
Laser single pulse: 1 ms-100 sec, Step 1 ms
Repeatable pulses 1 ms-100 sec with interval between pulses: 1 ms-2000 sec
2) Arbitrary shape laser pulse built from 100 elements. Each element has duration and initial and final current. Arbitrary shape pulse could be single or repeatable (see FIGS. 10, 11, 13, 14, 15).
3) Each arbitrary and standard pulse regime has Trigger In and Trigger Out synchronic pulses with tunable delay. For manual access to the device Trigger In option switch off for access via PC switch on. Trigger IN and Out input and output have separate BNC connectors on back side of the device,
4) Aiming beam has a fast driver rise/fall time of green (red, blue) laser (diodes) better that 1 micro-seconds. Driver currents of aiming beam are up to 300 mA. Voltages are up to 5 V for a blue laser. Switch off/on time is less than 1.0 microsecond. The power of aiming beam is of 0.5-10 m.
5) Two ADC inputs are connected on the back panel through DB9 connector.
6) Control Voltage on input Pulse Length Timer Stop (Pulse Length Timer Stop input (TTL, active high)) and input Stop the laser input (shuts down the laser) (TTL, active low are located on back panel through a separate DB9 connector.
7) Standard square wave temperature controlled pulses. The pulse duration is from 10 ms to 100 sec, step from 1 ms to 10 sec and pulse temperature from 35 C to 100 C, with accuracy +/−0.5 C are set-up for single individual pulse or repeatable pulses. In the case where average temperature must be constant, the temperature of 35 to 75 C with accuracy +/−0.1 C with integration time from 100 ms to 10 sec are set up each 1 to 100 ms. The temperature of irradiated object is measured by a thermo-sensor. The difference in between set-up temperature and measured temperature is measured by digital comparator and applied to a driver as a diode laser pump current. The time of temperature stabilization is about 5% of the pulse duration.

The set of commands is for following:
a) Arbitrary shape of pulses,
b) Measurement of the number of applied pulses for repetitive pulses when lasing is terminated,
c) Measurement of the pulse duration of single pulses when lasing is terminated, and
d) Reading all parameters of applied pulses: power, current, pulse shape, pulse duration, interstimulus intervals, trigger pulses delays, power of aiming beam, pulse duration of aiming beam, temperature of irradiated objects and
e) Temperature feedback.

While the present invention has been described in terms of specific embodiments, persons skilled in the art will recognize that many modifications and additions could be made to the specific embodiments without departing from the basic principals of the invention. For example many different wavelengths could be utilized if they the absorption in skin is within the range of about 0.25 cm$^{-1}$ to 10 cm$^{-1}$. Fiber optics with core diameters in the range of 5 to 100 microns are good for transmitting the laser pulses. Pulse shapes such as the following are good shapes for many experiments:

1. Increasing of power for pulse duration 50-150 ms from power level of 0.5 W with step less than 0.2 W with a diameter of irradiation area 0.5-2 mm lead to produce clear monomodal (single) pin prick pain and selective activation of A delta fibers.
2. Increasing of pulse duration from 0.3 to 20 sec with power level around 1.5 W with a diameter of irradiation area 5 mm-15 mm lead to inducing of clear monomodal hot pain and selective activation of C fibers.
3. Increasing of power for pulse duration of 400 to 2000 ms with a diameter of irradiated area 3-5 mm may induce clear single hot pain or clear single warmth sensation and selective activation of C fibers.

Therefore, the scope of the invention should be determined by the appended claims and their legal equivalents.

What is claimed is:

1. A local analgesia and pain relief treatment process for stimulating nerves to deactivate TRPV1 or TRPV2 positive nerve cells, comprising steps of:
   A) generating pulses of infrared light with a diode laser,
   B) directing said pulses to illuminate a target skin region containing at least one or more TRPV1 or TRPV2 positive nerve cells, to deliver laser energy to the target skin region producing measurable temperature increases in the skin surface temperature in response to each pulse defining for each pulse a maximum skin surface temperature,
   C) monitoring the skin surface temperature of the target skin region with an infrared temperature sensor, and
   D) controlling said diode laser to produce multiple laser pulses with duration of between 50 and 200 ms and repetition rates between 0.1 and 4 pulses per second and with pulse energies chosen to apply sufficient heat energy in the target skin region to maintain the maximum surface temperature of the target skin region at approximately 70 C to 75 C for at least nine seconds, producing controlled pain in the target skin region to thereby deactivate the TRPV1 or TRPV2 positive nerve cells to provide local analgesia or pain relief to the illuminated skin region.

2. The process as in claim 1 wherein said infrared light is infrared light at wavelengths of about 980 nm.

3. The process as in claim 2 wherein said nerves are C fiber nociceptors.

4. The process as in claim 3 wherein said nerves are A-delta fiber nociceptors.

5. The process as in claim 1 and further comprising a laser controller wherein said temperature sensor is configured to provide a temperature signal to said controller and said controller is programmed to utilize said temperature to provide feedback control of said laser in order to provide a desired temperature-time profile at said target skin region.

6. The process as in claim 5 wherein said time-temperature profile generates a time-temperature profile in the target skin region in a range 42 C to 50 C to evoked threshold burning pain and deactivate C fibers.

7. The process as in claim 5 wherein said time-temperature profile generates a time-temperature profile in the target skin region in a temperature range above 42 C.

8. The process as in claim 5 wherein said temperature-time profile is achieved output with a power of 1 to 50 W to permit deactivation of heat sensitive single nerve fibers or group fibers.

9. The process of claim 1 and further comprising the steps of increasing of power for pulse duration 5- 150 ms from power level of 0.5 W with step less than 0.2 W with a diameter of irradiation area 0.5-2 mm lead to produce threshold pin prick pain and follow up deactivation of A delta fibers.

10. The process as in claim 1 wherein said infrared light is infrared light having a wavelength in the range of 800 nm to 1.9 microns.

* * * * *